United States Patent [19]

Schneider et al.

[11] Patent Number: 5,503,978
[45] Date of Patent: Apr. 2, 1996

[54] METHOD FOR IDENTIFICATION OF HIGH AFFINITY DNA LIGANDS OF HIV-1 REVERSE TRANSCRIPTASE

[75] Inventors: Daniel J. Schneider; Larry Gold, both of Boulder, Colo.; Juli Feigon, Los Angeles, Calif.

[73] Assignee: University Research Corporation, Boulder, Colo.

[21] Appl. No.: 238,863

[22] Filed: May 6, 1994

Related U.S. Application Data

[63] Continuation-in-part of Ser. No. 714,131, Jun. 10, 1991, which is a continuation-in-part of Ser. No. 536,428, Jun. 11, 1990, abandoned, and a continuation-in-part of Ser. No. 964,624, Oct. 21, 1992.

[51] Int. Cl.$^6$ .............................. C12Q 1/68; C12P 19/34
[52] U.S. Cl. ................................. 435/6; 435/91.2
[58] Field of Search ........................................ 435/6, 91.2

[56] References Cited

U.S. PATENT DOCUMENTS

| | | | |
|---|---|---|---|
| 4,833,092 | 5/1989 | Geysen | 435/6 |
| 5,133,866 | 7/1992 | Kauvar | 435/6 |
| 5,270,163 | 12/1993 | Gold et al. | 435/6 |

FOREIGN PATENT DOCUMENTS

| | | |
|---|---|---|
| 2183661 | 6/1987 | United Kingdom. |
| WO89/06694 | 7/1989 | WIPO. |
| WO91/19813 | 12/1991 | WIPO. |

OTHER PUBLICATIONS

Joyce (1989) Gene 82:83.
Joyce and Inoue (1989) Nucleic Acids Research 17:711.
Ellington and Szostak (1990) Abstract of papers presented at the 1990 meeting on RNA Processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Arnold et al. (1992) Nature 357:85.
Baltimore (1970) Nature 226:1209.
Carey et al. (1983) Biochemistry 22: 2601.
Davies et al. (1991) Science 252:88.
Gilboa et al. (1979) Cell 18:93.
Huang et al. (1990) J. Biol. Chem. 265:11914.
Irvine et al. (1991) J. Mol. Biol. 222:739.
Jaeger et al. (1989) Proc. Natl. Acad. Sci. USA 86:7706.
Jocobo–Molina et al. (1993) Proc. Natl. Acad. Sci. USA 90:6320.
Kedar et al. (1990) Biochemistry 29:3603.
Kohlstaedt et al. (1992) Science 256:1783.
Kopp et al. (1991) Nuc. Acids. Res. 19(11):3035.
Krug and Berger (1991) Biochemistry 30:10614.
Lowary and Uhlenbeck (1987) Nucleic Acids Res. 15:10483.
Marshall and Caruthers (1993) Science 259:1564.
Merluzzi et al. (1990) Science 250:1411.
Nakane and Ono (1990) Biochemistry 29:2841.
Pauwels et al. (1990) Nature 343:470.
Peliska and Benkovic (1992) Science 258:1112.
Schneider et al. (1993) FASEB 7:201.
Temin and Mizutani (1970) Nature 226:1211.
Tuerk and Gold (1990) Science 249:505.
Tuerk et al. (1992) Proc. Natl. Acad. Sci. USA 89:6988.
Yarus and Berg (1970) Anal. Biochem. 35:450.
Zuker (1989) Science 244:48.

*Primary Examiner*—Stephanie W. Zitomer
*Attorney, Agent, or Firm*—Swanson & Bratschun

[57] ABSTRACT

Methods are described for the identification and preparation of DNA ligands to the HIV-1 reverse transcriptase protein. The invention encompasses specific ssDNA ligands to HIV-1 reverse transcriptase identified by the SELEX method including ssDNA ligands that inhibit the activity of HIV-1 reverse transcriptase.

3 Claims, 26 Drawing Sheets

| | | SEQ ID NO |
|---|---|---|
| 1 | 5'- CCCCTGCAGGTGATTTGCTCAAGT - 35N - AGTATCGCTAATCAGGCGGAT -3'<br>[ 35N TEMPLATE OLIGO ] | 1 |
| 2 | 5'- ATCCGCCTGATTAGCGATACT -3'<br>[ UPSTREAM PCR PRIMER ] | 2 |
| 3 | 5'- BBB-CCCCTGCAGGTGATTTGCTCAAGT -3'<br>[ BIOTINYLATED DOWNSTREAM PCR PRIMER AND DOWNSTREAM CLONING PRIMER ] | 3 |
| 4 | 5'- CCGAAGCTTAATACGACTCACTATAGGGATCCGCCTGATTAGCGATACT -3'<br>[ UPSTREAM CLONING PRIMER ] | 4 |
| 5 | 5'- TTCACACAGGAAACAG -3'<br>[ DNA SEQUENCING PRIMER ] | 5 |

| | 60 | 61 | 62 | 63 | 64 | 65 | 66 | 67 | 68 | 69 | 70 | 71 | 72 |
|---|---|---|---|---|---|---|---|---|---|---|---|---|---|
| 8, 17, 22, 30 | AGCCAGTCAAGTTAATGGTGCCAT | GCACAAGCA | | | | | | | | | | | |
| 3 | AATCGCCTTGTTTCGTTCGGTG | TTTAGCAGCGAA | | | | | | | | | | | |
| 11 | CAGGGTGCCGCTCAATTCTGGTGCCTT | GCAGAAG | | | | | | | | | | | |
| 42 | | CCAGGGTGCATCACGGGACTTACTCTAGCA | | | | | | | | | | | |
| 4 | TTAGCAAAG | TTCAAGC | CCGACTAACAAGCTCTACG | | | | | | | | | | |
| 37 | CTAGCAGAG | TAGAAGC | CGGACGATATGATGAT | | | | | | | | | | |
| 19 | GGACTCCCAG | TTCATCCGGTC | TTTATCACCTCC | | | | | | | | | | |
| 34, 36 | AAGCTCTTAG | TTGATGCGGTCAAATTTAAGCT | | | | | | | | | | | |
| 7, 39 | GAAAGCTCTTTTAG | T | GATCGTGACCAGTCCCTT | | | | | | | | | | |
| 44 | GGCTCAGTTGA | G | CGG | GACTTAATTGTTATT | | | | | | | | | |
| 16 | GATATACTTATTA | CTT | CCCACGGCTAACCAGACC | | | | | | | | | | |
| 1, 29 | | CAGAAGGATAAACTGTCCAGAACTTCGAATATATC | | | | | | | | | | | |
| 25 | CTCGAGGTGATCAGAAGGATTAAACCGGGGCT | | | | | | | | | | | |

FIG. 4B

SEQ ID NO:71
FIG. 5A

SEQ ID NO:64
FIG. 5B

RT6

```
    A   C                                              A
  G   T A                    T T A G G A A A          G  A C T T G
  C   A T   T C A G G  G  C G T C G A A A   G C A G G  T G G        G
  G       T A G T C C G C                   C G T C C  A C T
              G                              A                A A A A C
              C
              T
              A                              G
            5'                               G
                                             G
                                             G 3'
```

SEQ ID NO:57
FIG. 5C

RT10

```
      G A T                                                         A
    T     T                                                       G    A
  C         A                                    C   C   A G   G A G T G C T  G
  C         G     A T A C T T A T T T G  G C A G G  G C  C G   C G T T C A T G A  C
  G         C                            C G T C C            
  G         C                             A    A     A     A G
                                          C                      A
                                         T A A
                               3' G G G A C G T C C
                                    C C T T G C A G G
```

SEQ ID NO:56
FIG. 5E

SEQ ID NO:48
FIG. 5F

SEQ ID NO:60
FIG. 5D

SEQ ID NO:44
FIG. 5G

SEQ ID NO:67
FIG. 5H

RT26

```
           A A
    C C C T       A G G T G A T
    G G G G A       T C C A C T A
           C G
```

Fragment of SEQ ID NO: 44

Fragment of SEQ ID NO: 71

Fragment of SEQ ID NO: 64

Fragment of SEQ ID NO: 60

Fragment of SEQ ID NO: 67

FIG. 6E

SEQ ID NO: 73

SEQ ID NO:
5'- GTCCC TGTTC GGGCG CCA-- ----- ---> -3' (DNA 18-mer)   74
3'- CAGGG ACAAG CCCGC GGUGA CGAUC UCUAA -5' (RNA 30-mer)   75
FIG. 10A
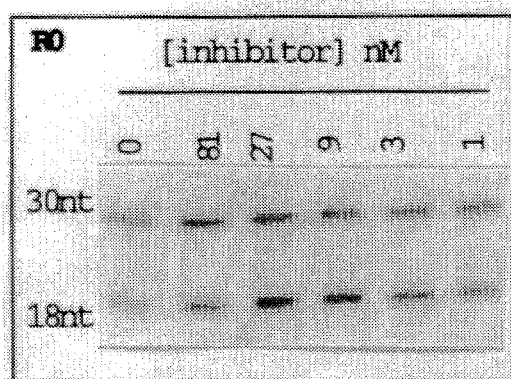
FIG. 10B
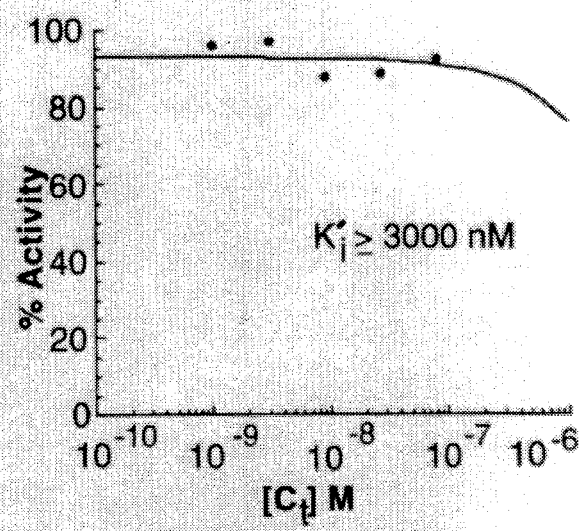
$K'_i \geq 3000$ nM
FIG. 10C
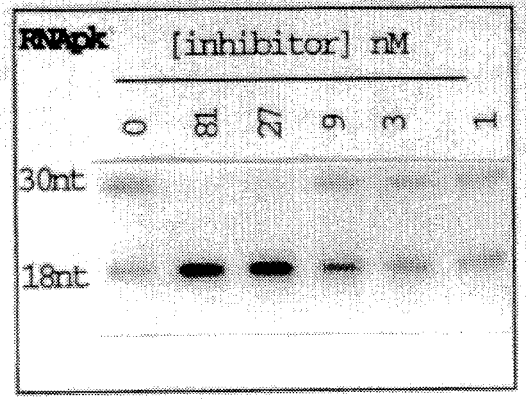
FIG. 10D
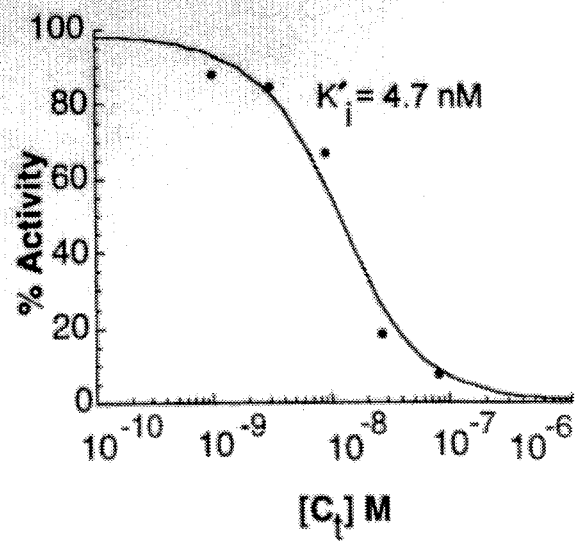
$K'_i = 4.7$ nM
FIG. 10E

| FRAGMENT | 5 | 10 | 15 | 20 | 25 | 30 | 35 | SEQ ID NO: |
|---|---|---|---|---|---|---|---|---|
| RT1 | CAGAAGGATAAACTGTCCAGAACTTGGAATATC | | | | | | | 71 |
| RT1A | CGGAAGGATATAGTGTCTACAACTACGGCTACGTC | | | | | | | 76 |
| RT1B | CAGACGGCGATAGTCGCCTAGCACGTGGACGATTC | | | | | | | 77 |
| RT1C | CGGAAGGATATACTGTCTCCGGAGAACTTGCAAGTGTC | | | | | | | 78 |
| RT1D | CAGAAGGATAAACCGTCGTCGGGGACTTGCAATGAATA | | | | | | | 79 |
| RT1E | CGGAAGGATAAAACGACACTGTCTAGAAACTTTGGAGTCCATC | | | | | | | 80 |
| RT1F | CGGAAGGATAAACTGTCGGGACAGAAACCCTTGGCATGTAGC | | | | | | | 81 |
| RT1G | CAGGAGGATAAACGACACTGTGAAGAAACTCGGCATGCGTAGC | | | | | | | 82 |
| RT1H | CAGTCGGATAAACTCCAAACTGTCCCAACCAATTCGCACTCATC | | | | | | | 83 |
| RT1I | CCGGAGGCTCAAACTGTCTAGAAACCACGAATTTCCC | | | | | | | 84 |
| RT1J | CGGAAGGATAAACTGTCGTGCCCAAACCGTTTTGGAATTTAGG | | | | | | | 85 |
| RT1K | CGGAAGGATAAGGCTTGCCAGCACTTGGAAGTCGTC | | | | | | | 86 |
| RT1L | CGGAAGGATAAACTGTCTCTAGAGCTTGGAATATT | | | | | | | 87 |
| RT1M | CAGAAGGATAAAAAGTGCCCACAGCCCTGGAATGTAAC | | | | | | | 88 |
| RT1N | CGGAAGGATAAAACTGCCTAGAAACGCGGAATATG | | | | | | | 89 |
| RT1O | CAGTAGGATAAACTGTCGAGATCGAGAACCTCGAATATGTC | | | | | | | 90 |
| RT1P | CAGAAGGATAAACTGTCGAGATCGAGAACCTCGAATATGTC | | | | | | | 91 |

SEQ ID NO: 92
FIG. 11B

```
                                    A A C
                                    G   T
                                    A   T
                                    C   G
                                    C   G
                                    T   A
              A A A A C T G   A T A T A T C A   G A   A A A
A  C     A A  G G A T                         C T T   G C A     T
G T A T C A G                                                 G G G   C G T   C
C A T A G T C  C C T A                                          G   A   C C A
G  A     C G
              RT1
```

SEQ ID NO: 71
FIG. 12A

```
         A A              AAACTGTCCAGAACTTGGA
A  C     AA
 TA TCAG GGAT
CAT AGTC CCTA
 G  A    CG
```
RT1t49

SEQ ID NO: 93
FIG. 12B

```
A  C     AA
 TA TCAG GGAT
CAT AGTC CCTA
 G  A    CG
```
RT1t30

SEQ ID NO: 94
FIG. 12C

SEQUENCE LISTING ( 1 ) GENERAL INFORMATION:

( i i i ) NUMBER OF SEQUENCES: 94

( 2 ) INFORMATION FOR SEQ ID NO:1:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
CCCCTGCAGG  TGATTTGCT  CAAGTNNNNN  NNNNNNNNN  NNNNNNNNNN  NNNNNNNNN     60
AGTATCGCTA  ATCAGGCGGA  T                                                81
```

( 2 ) INFORMATION FOR SEQ ID NO:2:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
ATCCGCCTGA  TTAGCGATAC  T                                                21
```

( 2 ) INFORMATION FOR SEQ ID NO:3:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i x ) FEATURE:
        ( A ) NAME/KEY: N
        ( B ) LOCATION: 1

( C ) OTHER INFORMATION: This symbol stands for biotinylated cytosine.

( x i ) SEQUENCE DESCRIPTION: SEQ ID NO:3:

NCCCTGCAGG TGATTTTGCT CAAGT　　　　　　　　　　　　　　　　　　　　　　　25

( 2 ) INFORMATION FOR SEQ ID NO:4:

( i ) SEQUENCE CHARACTERISTICS:
        ( A ) LENGTH: 49
        ( B ) TYPE: nucleic acid
        ( C ) STRANDEDNESS: single
        ( D ) TOPOLOGY: linear ( x i ) SEQUENCE DESCRIPTION: SEQ ID NO:4:

CCGAAGCTTA ATACGACTCA CTATAGGGAT CCGCCTGATT AGCGATACT　　　　　　　　　49

( 2 ) INFORMATION FOR SEQ ID NO:5:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( x i ) SEQUENCE DESCRIPTION: SEQ ID NO:5:

TTCACACAGG AAACAG　　　　　　　　　　　　　　　　　　　　　　　　　　　　16

( 2 ) INFORMATION FOR SEQ ID NO:6:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:6:

ATCCGCCTGA TTAGCGATAC TCAGGCTCCT GAGTGAAGTG CGGACATGTA CCNNNNACTT　　　60

GAGCAAAATC ACCTGCAGGG G　　　　　　　　　　　　　　　　　　　　　　　　81

( 2 ) INFORMATION FOR SEQ ID NO:7:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:7:

ATCCGCCTGA TTAGCGATAC TCGCCAGGCC CCTGTAGTCG GGCGGAGTCA NNNNNNACTT　　　60

GAGCAAAATC ACCTGCAGGG G　　　　　　　　　　　　　　　　　　　　　　　　81

( 2 ) INFORMATION FOR SEQ ID NO:8:

( i ) SEQUENCE CHARACTERISTICS:
        ( A ) LENGTH: 82
        ( B ) TYPE: nucleic acid
        ( C ) STRANDEDNESS: single
        ( D ) TOPOLOGY: linear ( x i ) SEQUENCE DESCRIPTION: SEQ ID NO:8:

ATCCGCCTGA TTAGCGATAC TCGTATAGGT CCCCTGCCGC TAAACAGCGC CGCGGTAACT　　　60

TGAGCAAAAT CACCTGCAGG GG　　　　　　　　　　　　　　　　　　　　　　　82

( 2 ) INFORMATION FOR SEQ ID NO:9:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:9:

ATCCGCCTGA TTAGCGATAC TCTGCCAGTC CCCTGTAATT AGACGGAAAC TCCTGTACTT    60

GAGCAAAATC ACCTGCAGGG G    81

( 2 ) INFORMATION FOR SEQ ID NO:10:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:10:

ATCCGCCTGA TTAGCGATAC TCAGCAGTCC CCCTATTCAT GGGCCCGCGG TTCATGACTT    60

GAGCAAAATC ACCTGCAGGG G    81

( 2 ) INFORMATION FOR SEQ ID NO:11:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:11:

ATCCGCCTGA TTAGCGATAC TTAACGCCAG GCCCCTGTAA TAGTGCGGAT CGACAGACTT    60

GAGCAAAATC ACCTGCAGGG G    81

( 2 ) INFORMATION FOR SEQ ID NO:12:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:12:

ATCCGCCTGA TTAGCGATAC TGAGCTGTTG TACAGTGCAA GTGTAGCAGT TCCCCTACTT    60

GAGCAAAATC ACCTGCAGGG G    81

( 2 ) INFORMATION FOR SEQ ID NO:13:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:13:

ATCCGCCTGA TTAGCGATAC TGTATCTTTA GTACAAGTGC TCGGCAGCTC CCCCACACTT    60

GAGCAAAATC ACCTGCAGGG G    81

( 2 ) INFORMATION FOR SEQ ID NO:14:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:14:

ATCCGCCTGA TTAGCGATAC TTCGCCAGTC CCCTGTTTCA GCGCGGATAT GACCATACTT    60

GAGCAAAATC ACCTGCAGGG G    81

( 2 ) INFORMATION FOR SEQ ID NO:15:

( i ) SEQUENCE CHARACTERISTICS:

(A) LENGTH: 80
(B) TYPE: nucleic acid
(C) STRANDEDNESS: single
(D) TOPOLOGY: linear (xi) SEQUENCE DESCRIPTION: SEQ ID NO:15:

ATCCGCCTGA TTAGCGATAC TGTATGGCTC TCAGCCCAGG CCCCTGATAC AGTCGACTTG    60

AGCAAAATCA CCTGCAGGGG    80

(2) INFORMATION FOR SEQ ID NO:16:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO:16:

ATCCGCCTGA TTAGCGATAC TGAAGAGCGT GCTGTCCCCT TAGGGTAATT GTCNNACTT    60

GAGCAAAATC ACCTGCAGGG G    81

(2) INFORMATION FOR SEQ ID NO:17:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO:17:

ATCCGCCTGA TTAGCGATAC TACGCGTGCT GCCCCATAAC GGTGGCTTCA ANNNNNACTT    60

GAGCAAAATC ACCTGCAGGG G    81

(2) INFORMATION FOR SEQ ID NO:18:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO:18:

ATCCGCCTGA TTAGCGATAC TGACAATGAG TCAAGTCGCG TGCTCCCCTG CTGTTGACTT    60

GAGCAAAATC ACCTGCAGGG G    81

(2) INFORMATION FOR SEQ ID NO:19:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO:19:

ATCCGCCTGA TTAGCGATAC TCGGGCCCCT GATTAACGCG CGCTGCCCCT CGGGTGACTT    60

GAGCAAAATC ACCTGCAGGG G    81

(2) INFORMATION FOR SEQ ID NO:20:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO:20:

ATCCGCCTGA TTAGCGATAC TCGATATGAG CGTGAGCGTG CTTCCCTTGT TGGTGNACTT    60

GAGCAAAATC ACCTGCAGGG G    81

( 2 ) INFORMATION FOR SEQ ID NO:21:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:21:

```
ATCCGCCTGA  TTAGCGATAC  TGTCTGTCAG  ATTCATGCGT  GCTCCCCCTT  CTGGTGACTT        60
GAGCAAAATC  ACCTGCAGGG  G                                                     81
```

( 2 ) INFORMATION FOR SEQ ID NO:22:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
ATCCGCCTGA  TTAGCGATAC  TCTGGAGCGT  GCTGCCCCTA  AAGGTGACTT  ACCAAGACTT        60
GAGCAAAATC  ACCTGCAGGG  G                                                     81
```

( 2 ) INFORMATION FOR SEQ ID NO:23:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
ATCCGCCTGA  TTAGCGATAC  TTAGCTACAC  TATATGGCGT  GCTCCCCCTG  TTCGTGACTT        60
GAGCAAAATC  ACCTGCAGGG  G                                                     81
```

( 2 ) INFORMATION FOR SEQ ID NO:24:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
ATCCGCCTGA  TTAGCGATAC  TCTTGGCCCG  TATTCGCGTG  CTGTCCCCCT  GAGATGACTT        60
GAGCAAAATC  ACCTGCAGGG  G                                                     81
```

( 2 ) INFORMATION FOR SEQ ID NO:25:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
ATCCGCCTGA  TTAGCGATAC  TGAACGTGCA  GCCCCCCGAA  ACGTGACTAG  CAANNNACTT        60
GAGCAAAATC  ACCTGCAGGG  G                                                     81
```

( 2 ) INFORMATION FOR SEQ ID NO:26:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:26:

ATCCGCCTGA TTAGCGATAC TGGATTTTTG TGCAAGCCCC CGAAAGCTGA TNNNNNACTT 60

GAGCAAAATC ACCTGCAGGG G 81

( 2 ) INFORMATION FOR SEQ ID NO:27:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:27:

ATCCGCCTGA TTAGCGATAC TACGTCAGGA CCCCTCATCG ATTTTCTTAA GNNNNNACTT 60

GAGCAAAATC ACCTGCAGGG G 81

( 2 ) INFORMATION FOR SEQ ID NO:28:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:28:

ATCCGCCTGA TTAGCGATAC TTTAGCAAAG GAGCCCCCGG ACTCAGATTA CNNNNNACTT 60

GAGCAAAATC ACCTGCAGGG G 81

( 2 ) INFORMATION FOR SEQ ID NO:29:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:29:

ATCCGCCTGA TTAGCGATAC TTGTTATAGT CCCCTGCCGC TGTTCTCGCG GGATTNACTT 60

GAGCAAAATC ACCTGCAGGG G 81

( 2 ) INFORMATION FOR SEQ ID NO:30:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:30:

ATCCGCCTGA TTAGCGATAC TCAAGTCAAA TCCCCTGACA GGAATTCCTT CCTGGAACTT 60

GAGCAAAATC ACCTGCAGGG G 81

( 2 ) INFORMATION FOR SEQ ID NO:31:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:31:

ATCCGCCTGA TTAGCGATAC TTGTTCAGTC CCCCTCTCAA GCTACTTTAC TTTGTAACTT 60

GAGCAAAATC ACCTGCAGGG G 81

( 2 ) INFORMATION FOR SEQ ID NO:32:

( i ) SEQUENCE CHARACTERISTICS:
        ( A ) LENGTH: 81
        ( B ) TYPE: nucleic acid ( C ) STRANDEDNESS: single
( D ) TOPOLOGY: linear ( x i ) SEQUENCE DESCRIPTION: SEQ ID NO:32:

ATCCGCCTGA TTAGCGATAC TAGCGAGCTT ATTAGAAGGA TAAACCGCCT ANNNNNACTT    60

GAGCAAAATC ACCTGCAGGG G    81

( 2 ) INFORMATION FOR SEQ ID NO:33:

( i ) SEQUENCE CHARACTERISTICS:
    ( A ) LENGTH: 81
    ( B ) TYPE: nucleic acid
    ( C ) STRANDEDNESS: single
    ( D ) TOPOLOGY: linear ( x i ) SEQUENCE DESCRIPTION: SEQ ID NO:33:

ATCCGCCTGA TTAGCGATAC TTGCTGGTCA TAGGTAAACA GCCCTGAGCT AACAGAACTT    60

GAGCAAAATC ACCTGCAGGG G    81

( 2 ) INFORMATION FOR SEQ ID NO:34:

( i ) SEQUENCE CHARACTERISTICS:
    ( A ) LENGTH: 81
    ( B ) TYPE: nucleic acid
    ( C ) STRANDEDNESS: single
    ( D ) TOPOLOGY: linear ( x i ) SEQUENCE DESCRIPTION: SEQ ID NO:34:

ATCCGCCTGA TTAGCGATAC TCAGAAGGAT AAACTGTCCA GAACATGGAA TATATCACTT    60

GAGCAAAATC ACCTGCAGGG G    81

( 2 ) INFORMATION FOR SEQ ID NO:35:

( i ) SEQUENCE CHARACTERISTICS:
    ( A ) LENGTH: 81
    ( B ) TYPE: nucleic acid
    ( C ) STRANDEDNESS: single
    ( D ) TOPOLOGY: linear ( x i ) SEQUENCE DESCRIPTION: SEQ ID NO:35:

ATCCGCCTGA TTAGCGATAC TATCGAGGTG ATCAGAAGGA TAAACCGCCG GGGCCTACTT    60

GAGCAAAATC ACCTGCAGGG G    81

( 2 ) INFORMATION FOR SEQ ID NO:36:

( i ) SEQUENCE CHARACTERISTICS:
    ( A ) LENGTH: 81
    ( B ) TYPE: nucleic acid
    ( C ) STRANDEDNESS: single
    ( D ) TOPOLOGY: linear ( x i ) SEQUENCE DESCRIPTION: SEQ ID NO:36:

ATCCGCCTGA TTAGCGATAC TCTAAACGGT GAAGGGTCTT TGCAGATGAA CAANNNACTT    60

GAGCAAAATC ACCTGCAGGG G    81

( 2 ) INFORMATION FOR SEQ ID NO:37:

( i ) SEQUENCE CHARACTERISTICS:
    ( A ) LENGTH: 81
    ( B ) TYPE: nucleic acid
    ( C ) STRANDEDNESS: single
    ( D ) TOPOLOGY: linear ( x i ) SEQUENCE DESCRIPTION: SEQ ID NO:37:

ATCCGCCTGA TTAGCGATAC TTTAGCAAAG TAGAAGCCGG TTAGAAGACC TAGAACACTT    60

GAGCAAAATC ACCTGCAGGG G    81

( 2 ) INFORMATION FOR SEQ ID NO:38:

(i) SEQUENCE CHARACTERISTICS:
    (A) LENGTH: 81
    (B) TYPE: nucleic acid
    (C) STRANDEDNESS: single
    (D) TOPOLOGY: linear (xi) SEQUENCE DESCRIPTION: SEQ ID NO:38:

ATCCGCCTGA TTAGCGATAC TTTAGCAAAG TTGAAGCCGG ACTAACAAGC TCTACGACTT   60

GAGCAAAATC ACCTGCAGGG G   81

(2) INFORMATION FOR SEQ ID NO:39:

(i) SEQUENCE CHARACTERISTICS:
    (A) LENGTH: 79
    (B) TYPE: nucleic acid
    (C) STRANDEDNESS: single
    (D) TOPOLOGY: linear (xi) SEQUENCE DESCRIPTION: SEQ ID NO:39:

ATCCGCCTGA TTAGCGATAC TGGGCTCAAG CTTGAGCGCG GCTCTCCACC TACGACTTGA   60

GCAAAATCAC CTGCAGGGG   79

(2) INFORMATION FOR SEQ ID NO:40:

(i) SEQUENCE CHARACTERISTICS:
    (A) LENGTH: 81
    (B) TYPE: nucleic acid
    (C) STRANDEDNESS: single
    (D) TOPOLOGY: linear (xi) SEQUENCE DESCRIPTION: SEQ ID NO:40:

ATCCGCCTGA TTAGCGATAC TTGTCGGGTG GCTTTAGCAG AGACAATATG CATTNNACTT   60

GAGCAAAATC ACCTGCAGGG G   81

(2) INFORMATION FOR SEQ ID NO:41:

(i) SEQUENCE CHARACTERISTICS:
    (A) LENGTH: 81
    (B) TYPE: nucleic acid
    (C) STRANDEDNESS: single
    (D) TOPOLOGY: linear (xi) SEQUENCE DESCRIPTION: SEQ ID NO:41:

ATCCGCCTGA TTAGCGATAC TCTATAACCA GGTTTCGGGT GCTTTAGCAA ANNNNNACTT   60

GAGCAAAATC ACCTGCAGGG G   81

(2) INFORMATION FOR SEQ ID NO:42:

(i) SEQUENCE CHARACTERISTICS:
    (A) LENGTH: 81
    (B) TYPE: nucleic acid
    (C) STRANDEDNESS: single
    (D) TOPOLOGY: linear (xi) SEQUENCE DESCRIPTION: SEQ ID NO:42:

ATCCGCCTGA TTAGCGATAC TGGGAGGGAG GGAGGGCCGT AGCTAATTAG GATCAAACTT   60

GAGCAAAATC ACCTGCAGGG G   81

(2) INFORMATION FOR SEQ ID NO:43:

(i) SEQUENCE CHARACTERISTICS:
    (A) LENGTH: 81
    (B) TYPE: nucleic acid
    (C) STRANDEDNESS: single
    (D) TOPOLOGY: linear (xi) SEQUENCE DESCRIPTION: SEQ ID NO:43:

ATCCGCCTGA TTAGCGATAC TACGCGTGCT GCCCCTAAAG GCGATTGTCG GATGTTACTT   60

GAGCAAAATC ACCTGCAGGG G    81

( 2 ) INFORMATION FOR SEQ ID NO:44:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:44:

ATCCGCCTGA TTAGCGATAC TTACGTGAGC GTGCTGTCCC CTAAAGGTGA TACGTCACTT    60

GAGCAAAATC ACCTGCAGGG G    81

( 2 ) INFORMATION FOR SEQ ID NO:45:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:45:

ATCCGCCTGA TTAGCGATAC TCTGGAGCGT GCTGCCCCTA AAGGTGACTT ACCAAGACTT    60

GAGCAAAATC ACCTGCAGGG G    81

( 2 ) INFORMATION FOR SEQ ID NO:46:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:46:

ATCCGCCTGA TTAGCGATAC TCGCGTGCTG CCCCTTAAGG TGATGGTGTA TATTCCACTT    60

GAGCAAAATC ACCTGCAGGG G    81

( 2 ) INFORMATION FOR SEQ ID NO:47:

( i ) SEQUENCE CHARACTERISTICS:
        ( A ) LENGTH: 79
        ( B ) TYPE: nucleic acid
        ( C ) STRANDEDNESS: single
        ( D ) TOPOLOGY: linear ( x i ) SEQUENCE DESCRIPTION: SEQ ID NO:47:

ATCCGCCTGA TTAGCGATAC TTCTCCGACT CAAAGCGCGT GCTCCCCTCC GGTGACTTGA    60

GCAAAATCAC CTGCAGGGG    79

( 2 ) INFORMATION FOR SEQ ID NO:48:

( i ) SEQUENCE CHARACTERISTICS:
        ( A ) LENGTH: 82
        ( B ) TYPE: nucleic acid
        ( C ) STRANDEDNESS: single
        ( D ) TOPOLOGY: linear ( x i ) SEQUENCE DESCRIPTION: SEQ ID NO:48:

ATCCGCCTGA TTAGCGATAC TCGTATAGGT CCCCTGCCGC TAAACAGCGC CGCGGTAACT    60

TGAGCAAAAT CACCTGCAGG GG    82

( 2 ) INFORMATION FOR SEQ ID NO:49:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:49:

ATCCGCCTGA TTAGCGATAC TGCCAGGTCC CCTGTAATTA GACGGAAACT ACCTGTACTT 60

GAGCAAAATC ACCTGCAGGG G 81

( 2 ) INFORMATION FOR SEQ ID NO:50:

( i ) SEQUENCE CHARACTERISTICS:
          ( A ) LENGTH: 81
          ( B ) TYPE: nucleic acid
          ( C ) STRANDEDNESS: single
          ( D ) TOPOLOGY: linear ( x i ) SEQUENCE DESCRIPTION: SEQ ID NO:50:

ATCCGCCTGA TTAGCGATAC TGCCAGGACC CCTGTAATCT GGCGTATTTC CCTGTTACTT 60

GAGCAAAATC ACCTGCAGGG G 81

( 2 ) INFORMATION FOR SEQ ID NO:51:

( i ) SEQUENCE CHARACTERISTICS:
          ( A ) LENGTH: 81
          ( B ) TYPE: nucleic acid
          ( C ) STRANDEDNESS: single
          ( D ) TOPOLOGY: linear ( x i ) SEQUENCE DESCRIPTION: SEQ ID NO:51:

ATCCGCCTGA TTAGCGATAC TCGCCAGTAC CCCTGTAAGT GGGCGGAAAC TCTAGTACTT 60

GAGCAAAATC ACCTGCAGGG G

2) INFORMATION FOR SEQ ID NO:52:

( i ) SEQUENCE CHARACTERISTICS:
          ( A ) LENGTH: 81
          ( B ) TYPE: nucleic acid
          ( C ) STRANDEDNESS: single
          ( D ) TOPOLOGY: linear ( x i ) SEQUENCE DESCRIPTION: SEQ ID NO:52:

ATCCGCCTGA TTAGCGATAC TTCGTCAGGA CCCCTGTAAA CAGGCGGGAT AATCTAACTT 60

GAGCAAAATC ACCTGCAGGG G 81

( 2 ) INFORMATION FOR SEQ ID NO:53:

( i ) SEQUENCE CHARACTERISTICS:
          ( A ) LENGTH: 80
          ( B ) TYPE: nucleic acid
          ( C ) STRANDEDNESS: single
          ( D ) TOPOLOGY: linear ( x i ) SEQUENCE DESCRIPTION: SEQ ID NO:53:

ATCCGCCTGA TTAGCGATAC TGGGCCCTCA GCTTGAGCGC GGACTACATA TTATCACTTG 60

AGCAAAATCA CCTGCAGGGG 80

( 2 ) INFORMATION FOR SEQ ID NO:54:

( i ) SEQUENCE CHARACTERISTICS:
          ( A ) LENGTH: 81
          ( B ) TYPE: nucleic acid
          ( C ) STRANDEDNESS: single
          ( D ) TOPOLOGY: linear ( x i ) SEQUENCE DESCRIPTION: SEQ ID NO:54:

ATCCGCCTGA TTAGCGATAC TGGGCCCTCA GCTTGAGCGC GGAATCACTA AGATACACTT 60

GAGCAAAATC ACCTGCAGGG G 81

( 2 ) INFORMATION FOR SEQ ID NO:55:

( i ) SEQUENCE CHARACTERISTICS:
          ( A ) LENGTH: 81

(B) TYPE: nucleic acid
(C) STRANDEDNESS: single
(D) TOPOLOGY: linear (xi) SEQUENCE DESCRIPTION: SEQ ID NO:55:

```
ATCCGCCTGA TTAGCGATAC TGGGCCCTCA GCTAGAGCCG GATTAAACAG TCTTCAACTT    60
GAGCAAAATC ACCTGCAGGG G                                              81
```

(2) INFORMATION FOR SEQ ID NO:56:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO:56:

```
ATCCGCCTGA TTAGCGATAC TTATTTGCCC TTGCAGGCCG CAGGAGTGCT AGCAGTACTT    60
GAGCAAAATC ACCTGCAGGG G                                              81
```

(2) INFORMATION FOR SEQ ID NO:57:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO:57:

```
ATCCGCCTGA TTAGCGATAC TCAGGCGTTA GGGAAGGGCG TCGAAAGCAG GGTGGGACTT    60
GAGCAAAATC ACCTGCAGGG G                                              81
```

(2) INFORMATION FOR SEQ ID NO:58:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO:58:

```
ATCCGCCTGA TTAGCGATAC TCAGGCGCCG GGGGGGTGGG AATACAGTGA TCAGCGACTT    60
GAGCAAAATC ACCTGCAGGG G                                              81
```

(2) INFORMATION FOR SEQ ID NO:59:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO:59:

```
ATCCGCCTGA TTAGCGATAC TCAGGCCTTG GGCGGGCCGG GACAATGGAG AGATTTACTT    60
GAGCAAAATC ACCTGCAGGG G                                              81
```

(2) INFORMATION FOR SEQ ID NO:60:

(i) SEQUENCE CHARACTERISTICS:
        (A) LENGTH: 80
        (B) TYPE: nucleic acid
        (C) STRANDEDNESS: single
        (D) TOPOLOGY: linear (xi) SEQUENCE DESCRIPTION: SEQ ID NO:60:

```
ATCCGCCTGA TTAGCGATAC TAGCCAGTCA AGTTAATGGG TGCCATGCAG AAGCAACTTG    60
AGCAAAATCA CCTGCAGGGG                                                80
```

( 2 ) INFORMATION FOR SEQ ID NO:61:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:61:

```
ATCCGCCTGA TTAGCGATAC TAATCGGCCT TGTTTCGGGG TGCTTTAGCA GAGGAAACTT      60

GAGCAAAATC ACCTGCAGGG G                                                81
```

( 2 ) INFORMATION FOR SEQ ID NO:62:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:62:

```
ATCCGCCTGA TTAGCGATAC TCAGGGTGCC GCTCAATTCT GGGTGCCTTG CAGAAGACTT      60

GAGCAAAATC ACCTGCAGGG G                                                81
```

( 2 ) INFORMATION FOR SEQ ID NO:63:

( i ) SEQUENCE CHARACTERISTICS:
        ( A ) LENGTH: 79
        ( B ) TYPE: nucleic acid
        ( C ) STRANDEDNESS: single
        ( D ) TOPOLOGY: linear ( x i ) SEQUENCE DESCRIPTION: SEQ ID NO:63:

```
ATCCGCCTGA TTAGCGATAC TCCAGCGGTG GCATCACGCG GACTTACTCT AGCAACTTGA      60

GCAAAATCAC CTGCAGGGG                                                   79
```

( 2 ) INFORMATION FOR SEQ ID NO:64:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:64:

```
ATCCGCCTGA TTAGCGATAC TTTAGCAAAG TTGAAGCCGG ACTAACAAGC TCTACGACTT      60

GAGCAAAATC ACCTGCAGGG G                                                81
```

( 2 ) INFORMATION FOR SEQ ID NO:65:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:65:

```
ATCCGCCTGA TTAGCGATAC TCTAGCAGAG TAGAAGCCGG ACGATATATC GATGATACTT      60

GAGCAAAATC ACCTGCAGGG G                                                81
```

( 2 ) INFORMATION FOR SEQ ID NO:66:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:66:

```
ATCCGCCTGA TTAGCGATAC TGGACTCCCA GTTGATGCGC GGTCTTTATC ACCTCCACTT    60

GAGCAAAATC ACCTGCAGGG G                                              81
```

( 2 ) INFORMATION FOR SEQ ID NO:67:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:67:

```
ATCCGCCTGA TTAGCGATAC TAAGCTCTTA GTTGATGCGC GGTCAAAATT TAAGCTACTT    60

GAGCAAAATC ACCTGCAGGG G                                              81
```

( 2 ) INFORMATION FOR SEQ ID NO:68:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:68:

```
ATCCGCCTGA TTAGCGATAC TGAAGCTCTT TTAGTGATGC GTGGACCAGT CCCCTTACTT    60

GAGCAAAATC ACCTGCAGGG G                                              81
```

( 2 ) INFORMATION FOR SEQ ID NO:69:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:69:

```
ATCCGCCTGA TTAGCGATAC TGGGCTCCAG CTTGAGCGGC GACTTAATTG GTTATTACTT    60

GAGCAAAATC ACCTGCAGGG G                                              81
```

( 2 ) INFORMATION FOR SEQ ID NO:70:

( i ) SEQUENCE CHARACTERISTICS:
        ( A ) LENGTH: 80
        ( B ) TYPE: nucleic acid
        ( C ) STRANDEDNESS: single
        ( D ) TOPOLOGY: linear ( x i ) SEQUENCE DESCRIPTION: SEQ ID NO:70:

```
ATCCGCCTGA TTAGCGATAC TGATATACTT ATTACTTCGC ACGGCTAACC AGACCACTTG    60

AGCAAAATCA CCTGCAGGGG                                                80
```

( 2 ) INFORMATION FOR SEQ ID NO:71:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:71:

```
ATCCGCCTGA TTAGCGATAC TCAGAAGGAT AAACTGTCCA GAACTTGGAA TATATCACTT    60

GAGCAAAATC ACCTGCAGGG G                                              81
```

( 2 ) INFORMATION FOR SEQ ID NO:72:

( i ) SEQUENCE CHARACTERISTICS:
        ( A ) LENGTH: 81
        ( B ) TYPE: nucleic acid
        ( C ) STRANDEDNESS: single (D) TOPOLOGY: linear (xi) SEQUENCE DESCRIPTION: SEQ ID NO:72:

ATCCGCCTGA TTAGCGATAC TCTCGAGGTG ATCAGAAGGA TAAACCGCCG GGGCCTACTT    60

GAGCAAAATC ACCTGCAGGG G    81

(2) INFORMATION FOR SEQ ID NO:73:

(i) SEQUENCE CHARACTERISTICS:
        (A) LENGTH: 28
        (B) TYPE: nucleic acid
        (C) STRANDEDNESS: single
        (D) TOPOLOGY: linear (xi) SEQUENCE DESCRIPTION: SEQ ID NO:73:

GGUCCGAAGU GCAACGGGAA AAUGCACU    28

(2) INFORMATION FOR SEQ ID NO:74:

(i) SEQUENCE CHARACTERISTICS:
        (A) LENGTH: 18
        (B) TYPE: nucleic acid
        (C) STRANDEDNESS: single
        (D) TOPOLOGY: linear (xi) SEQUENCE DESCRIPTION: SEQ ID NO:74:

GTCCCTGTTC GGGCGCCA    18

(2) INFORMATION FOR SEQ ID NO:75:

(i) SEQUENCE CHARACTERISTICS:
        (A) LENGTH: 30
        (B) TYPE: nucleic acid
        (C) STRANDEDNESS: single
        (D) TOPOLOGY: linear (xi) SEQUENCE DESCRIPTION: SEQ ID NO:75:

CAGGGACAAG CCCGCGGUGA CGAUCUCUAA    30

(2) INFORMATION FOR SEQ ID NO:76:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO:76:

ATCCGCCTGA TTAGCGATAC TCGGAAGGAT ATAGTGTCTA CAACTACGGC TACGTCACTT    60

GAGCAAAATC ACCTGCAGGG G    81

(2) INFORMATION FOR SEQ ID NO:77:

(i) SEQUENCE CHARACTERISTICS:
        (A) LENGTH: 81
        (B) TYPE: nucleic acid
        (C) STRANDEDNESS: single
        (D) TOPOLOGY: linear (xi) SEQUENCE DESCRIPTION: SEQ ID NO:77:

ATCCGCCTGA TTAGCGATAC TCAGACGGCG AGTCGGCCTA GCACGTGGAC GATTTCACTT    60

GAGCAAAATC ACCTGCAGGG G    81

(2) INFORMATION FOR SEQ ID NO:78:

(i) SEQUENCE CHARACTERISTICS:
        (A) LENGTH: 81
        (B) TYPE: nucleic acid
        (C) STRANDEDNESS: single
        (D) TOPOLOGY: linear ( x i ) SEQUENCE DESCRIPTION: SEQ ID NO:78:

ATCCGCCTGA TTAGCGATAC TCGGAAGGAT ATACTGTCTA GAACTTGGAA AGTGTCACTT    60

GAGCAAAATC ACCTGCAGGG G    81

( 2 ) INFORMATION FOR SEQ ID NO:79:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:79:

ATCCGCCTGA TTAGCGATAC TCAGAAGGAT AAACCGTCCG GGACTTGCAA TGAATAACTT    60

GAGCAAAATC ACCTGCAGGG G    81

( 2 ) INFORMATION FOR SEQ ID NO:80:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:80:

ATCCGCCTGA TTAGCGATAC TCGGAAGGAT AAACTGTCTA GAACTTGGAG TCCATCACTT    60

GAGCAAAATC ACCTGCAGGG G    81

( 2 ) INFORMATION FOR SEQ ID NO:81:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:81:

ATCCGCCTGA TTAGCGATAC TCGGAAGGAT ACACTGTCTA GAACCTAGAG TACGTCACTT    60

GAGCAAAATC ACCTGCAGGG G    81

( 2 ) INFORMATION FOR SEQ ID NO:82:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:82:

ATCCGCCTGA TTAGCGATAC TCAGGAGGAA CGACGGGACA GACCTTGGCA TGTAGCACTT    60

GAGCAAAATC ACCTGCAGGG G    81

( 2 ) INFORMATION FOR SEQ ID NO:83:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:83:

ATCCGCCTGA TTAGCGATAC TCAGTCGGCC AAACTGTGAA GAACTCGGAC GCCCTCACTT    60

GAGCAAAATC ACCTGCAGGG G    81

( 2 ) INFORMATION FOR SEQ ID NO:84:

( i ) SEQUENCE CHARACTERISTICS:
        ( A ) LENGTH: 81

( B ) TYPE: nucleic acid
( C ) STRANDEDNESS: single
( D ) TOPOLOGY: linear ( x i ) SEQUENCE DESCRIPTION: SEQ ID NO:84:

ATCCGCCTGA TTAGCGATAC TCCGGAGGCT CAACTGTCCA GCAATTCGCA CTCATCACTT    60

GAGCAAAATC ACCTGCAGGG G    81

( 2 ) INFORMATION FOR SEQ ID NO:85:

( i ) SEQUENCE CHARACTERISTICS:
      ( A ) LENGTH: 81
      ( B ) TYPE: nucleic acid
      ( C ) STRANDEDNESS: single
      ( D ) TOPOLOGY: linear ( x i ) SEQUENCE DESCRIPTION: SEQ ID NO:85:

ATCCGCCTGA TTAGCGATAC TCGGAAGGAT AAACTGTCTA GAACCACGAA TTTCCCACTT    60

GAGCAAAATC ACCTGCAGGG G    81

( 2 ) INFORMATION FOR SEQ ID NO:86:

( i ) SEQUENCE CHARACTERISTICS:
      ( A ) LENGTH: 81
      ( B ) TYPE: nucleic acid
      ( C ) STRANDEDNESS: single
      ( D ) TOPOLOGY: linear ( x i ) SEQUENCE DESCRIPTION: SEQ ID NO:86:

ATCCGCCTGA TTAGCGATAC TCAGAAGGAT AGGCTGCCTA GAGCTTGGAA TTTAGGACTT    60

GAGCAAAATC ACCTGCAGGG G    81

( 2 ) INFORMATION FOR SEQ ID NO:87:

( i ) SEQUENCE CHARACTERISTICS:
      ( A ) LENGTH: 81
      ( B ) TYPE: nucleic acid
      ( C ) STRANDEDNESS: single
      ( D ) TOPOLOGY: linear ( x i ) SEQUENCE DESCRIPTION: SEQ ID NO:87:

ATCCGCCTGA TTAGCGATAC TCGGAAGGAT AAACAGCCCT GAGCTTGGAA GTCGTCACTT    60

GAGCAAAATC ACCTGCAGGG G    81

( 2 ) INFORMATION FOR SEQ ID NO:88:

( i ) SEQUENCE CHARACTERISTICS:
      ( A ) LENGTH: 81
      ( B ) TYPE: nucleic acid
      ( C ) STRANDEDNESS: single
      ( D ) TOPOLOGY: linear ( x i ) SEQUENCE DESCRIPTION: SEQ ID NO:88:

ATCCGCCTGA TTAGCGATAC TCAGAAGGAT AAACTGTCTA GAACTTGGAA TATATTACTT    60

GAGCAAAATC ACCTGCAGGG G    81

( 2 ) INFORMATION FOR SEQ ID NO:89:

( i ) SEQUENCE CHARACTERISTICS:
      ( A ) LENGTH: 81
      ( B ) TYPE: nucleic acid
      ( C ) STRANDEDNESS: single
      ( D ) TOPOLOGY: linear ( x i ) SEQUENCE DESCRIPTION: SEQ ID NO:89:

ATCCGCCTGA TTAGCGATAC TCGGAAGGAT AAAGTGCCCA CAGCCTGGAA TGTAACACTT    60

GAGCAAAATC ACCTGCAGGG G    81

( 2 ) INFORMATION FOR SEQ ID NO:90:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:90:

```
ATCCGCCTGA TTAGCGATAC TCAGTAGGAT AAACTGTCTA GAACGCGGAA GATATGACTT        60

GAGCAAAATC ACCTGCAGGG G                                                 81
```

( 2 ) INFORMATION FOR SEQ ID NO:91:

( i ) SEQUENCE CHARACTERISTICS:
        ( A ) LENGTH: 81
        ( B ) TYPE: nucleic acid
        ( C ) STRANDEDNESS: single
        ( D ) TOPOLOGY: linear ( x i ) SEQUENCE DESCRIPTION: SEQ ID NO:91:

```
ATCCGCCTGA TTAGCGATAC TCAGAAGGAT AAACTGTCGA GAACCTCGAA TATGTCACTT        60

GAGCAAAATC ACCTGCAGGG G                                                 81
```

( 2 ) INFORMATION FOR SEQ ID NO:92:

( i ) SEQUENCE CHARACTERISTICS:
        ( A ) LENGTH: 56
        ( B ) TYPE: nucleic acid
        ( C ) STRANDEDNESS: single
        ( D ) TOPOLOGY: linear ( x i ) SEQUENCE DESCRIPTION: SEQ ID NO:92:

```
ATCCGCCTGA TTAGCGATAC TCGGNAGGAN ANNCNGNNTN GNNCNNNGNN NNCNNN           56
```

( 2 ) INFORMATION FOR SEQ ID NO:93:

( i ) SEQUENCE CHARACTERISTICS:
        ( A ) LENGTH: 49
        ( B ) TYPE: nucleic acid
        ( C ) STRANDEDNESS: single
        ( D ) TOPOLOGY: linear ( x i ) SEQUENCE DESCRIPTION: SEQ ID NO:93:

```
ATCCGCCTGA ATAGCGATAC TCAGAAGGAT AAACTGTCCA GAACTTGGA                   49
```

( 2 ) INFORMATION FOR SEQ ID NO:94:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO:94:

```
ATCCGCCTGA ATAGCGATAC TCAGAAGGAT                                        30
```

METHOD FOR IDENTIFICATION OF HIGH AFFINITY DNA LIGANDS OF HIV-1 REVERSE TRANSCRIPTASE

This work was partially supported by a grant from the United States Government funded through the National Institutes of Health. The U.S. Government may have certain rights in this invention.

RELATED APPLICATIONS

This application is a Continuation-in-Part of U.S. patent application Ser. No. 07/714,131, filed Jun. 10, 1991, entitled Nucleic Acid Ligands, which is a Continuation-in-Part of U.S. patent application Ser. No. 07/536,428, filed Jun. 11, 1990, entitled Systematic Evolution of Ligands by Exponential Enrichment, now abandoned, and U.S. patent application Ser. No. 07/964,624, filed Oct. 21, 1992, entitled Methods of Producing Nucleic Acid Ligands.

FIELD OF THE INVENTION

Described herein are methods for identifying and preparing high-affinity DNA ligands to HIV-1 Reverse Transcriptase (RT). The method utilized herein for identifying such DNA ligands is called SELEX, an acronym for Systematic Evolution of Ligands by EXponential enrichment. Specifically disclosed herein are high-affinity single-stranded DNA ligands. The invention includes high-affinity ssDNA inhibitors of HIV-1 RT. The invention also includes suicide inhibitors of HIV-1 RT.

BACKGROUND OF THE INVENTION

The reverse transcriptase (RT) of Type 1 Human Immunodeficiency Virus (HIV-1) plays an indispensable role in the life cycle of the virus. Its premier function is the synthesis of a double-stranded DNA copy of the RNA genome for integration into the host chromosome. This is achieved by the concerted application of a number of innate activities including minus-strand DNA synthesis via an RNA-dependent DNA polymerase activity, concomitant degradation of the template RNA strand via an RNase H activity, and plus-strand DNA synthesis via a DNA-dependent DNA polymerase activity (Baltimore, D. (1970) Nature 226:1209; Temin, H. M. and Mizutani, S. (1970) Nature 226:1211; Gilboa, E. et al. (1979) Cell 18:93–100; Goff, S. P. (1990) J. Acq. Imm. Defic. Syndr. 3:93–100; Peliska, J. A. and Benkovic, S. J. (1992) Science 258:1112–1118). Because the cells HIV-1 infects contain no endogenous RT, it must also possess a mechanism to ensure its packaging into the mature viral particle to guarantee its presence in the succeeding infection.

HIV-1 is generally accepted as the etiological agent of Acquired Immune Deficiency Syndrome (AIDS). The importance of its function in the life cycle of HIV-1 and the lack of a natural function in the host cell make RT a preferred target for antiviral agents.

Several types of HIV-1 RT inhibitors are known. Many, such as AZT (3'-azido-2',3'-dideoxythymidine), are nucleoside analogs, which when incorporated into polynucleotides by HIV-1 RT, result in chain termination. (Kedar, P. S. et al. (1990) Biochem, 29:3603–3611; Huang, P. et al. (1990) J. Biol. Chem. 265:11914–11918). Other nucleoside analogs that inhibit HIV-1 RT include ddC (2',3'-dideoxycytidine) and ddI (2',3'-dideoxyinosine) Inhibitors that are not nucleoside analogs have also been described. These include dipyridodiazepinones (e.g., Merluzzi, V. J. et al. (1990) Science 250:1411–1413; Kopp, E. B. et al. (1991) Nuc. Acids Res. 19(11):3035–3039), tetrahydro-imidazo[4,5,1-jk][1,4]-benzodiazepin- 2(1H)-one and -thione (TIBO) derivatives (e.g., Pauwels, T. et al. (1990) Nature 343:470–474), and catechin derivatives (e.g., Nakane, H., and Ono, K. (1990) Biochem. 29:2841–2845). These nonnucleosides inhibit by mechanisms other than direct competition for substrate binding sites (Kopp, E. B. et al. (1991) Nuc. Acids Res. 19(11): 3035–3039).

A family of phosphorodithioate-linked ssDNA nucleotides have been described with the property of inhibiting HIV-1 RT activity at $K_i$ values ranging from 0.5–180 nM (Marshall and Caruthers, (1993), Science 259:1564–1570). The specific sequences of these nucleotides were based on the sequence of various nucleic acid substrates of HIV-RT.

RNA pseudoknots that bind specifically to the polymerase active site of HIV-1 RT and inhibit the RNA-dependent DNA polymerase activity have already been identified using SELEX (U.S. patent application Ser. No. 07/964,624, which is specifically incorporated herein by reference; Tuerk, C. et al. (1992) Proc. Natl. Acad. Sci., U.S.A. 89:6988–6992).

The development of high affinity DNA ligands capable of inhibiting HIV-1 reverse transcriptase would be useful in the treatment of Type 1 Human Immunodeficiency Virus. Herein described are high affinity ssDNA ligand inhibitors of HIV-1 reverse transcriptase.

BRIEF SUMMARY OF THE INVENTION

The present invention includes methods of identifying and producing DNA ligands to HIV-1 RT and the DNA ligands so identified and produced. Specifically, ssDNA sequences are provided that are capable of binding specifically to HIV-1 RT. Included within the invention are the ssDNA ligand sequences shown in FIGS. 3 and 4.

Also included in this invention are DNA ligands of HIV-1 RT that are inhibitors of HIV-1 RT. Specifically, ssDNA ligands are identified and described which inhibit the RNA-dependent DNA polymerase activity of HIV-1 RT.

Further included in this invention is a method of identifying DNA ligands and DNA ligand sequences to HIV-1 RT comprising the steps of (a) preparing a candidate mixture of nucleic acids, (b) partitioning between members of said candidate mixture on the basis of affinity to HIV-1 RT, and (c) amplifying the selected molecules to yield a mixture of nucleic acids enriched for nucleic acid sequences with a relatively higher affinity for binding to HIV-1 RT.

More specifically, the present invention includes the ssDNA ligands to HIV-1 RT identified according to the above-described method, including those ligands listed in FIGS. 3 and 4. Also included are ssDNA ligands to HIV-1 RT that are substantially homologous to any of the given ligands and that have substantially the same ability to bind and inhibit HIV-1 RT. Further included in this invention are ssDNA ligands to HIV-1 RT that have substantially the same structural form as the ligands presented herein and that have substantially the same ability to bind and inhibit HIV-1 RT.

Further included in this invention are ssDNA ligands incorporating at specific positions nucleotide analogs possessing a reactive group able to covalently crosslink the ligand to HIV-1 RT upon binding. This invention also includes the ligands as described above, wherein covalent crosslinking is coupled to the activity of the HIV-1 RT.

The present invention also includes modified nucleotide sequences based on the DNA ligands identified herein and mixtures of the same.

BRIEF DESCRIPTION OF THE FIGURES

FIGS. 1A and 1B show the experimental design and oligonucleotide sequences used in generating the candidate mixture of ssDNA. A degenerate double-stranded DNA library was created using the Polymerase Chain Reaction to amplify oligo 1, using oligos 2 and 3 as primers. Box 1 shows the 35N template oligo (oligo 1) (SEQ ID NO:1), Box 2 shows the upstream PCR primer (oligo 2) (SEQ ID NO:2), Box 3 shows the biotinylated downstream PCR primer (oligo 3) (SEQ ID NO:3) and downstream cloning primer (oligo 3 with biotins removed), Box 4 shows the upstream cloning primer (oligo 4) (SEQ ID NO:4), and Box 5 shows the DNA sequencing primer (oligo 5) (SEQ ID NO:5).

FIGS. 3A and 3B show sequences isolated from the library after cycle 12 (SEQ ID NOS:6–42). The top of the Figure shows the upstream PCR primer (see FIG. 1B) and the complement of the downstream PCR primer and downstream cloning primer (see FIG. 1). Only the 35 positions originally randomized are shown below for each numbered individual. However, the full-length sequence includes the upstream and downstream sequences as shown at the top of the Figure. Isolates were grouped and aligned by common primary sequence elements. Clones are indicated by number. Approximately 3 of 4 selected ligands contained the sequence CCCCT (boxed), or a variant of this pentamer. Other regions of similarity among isolates are shaded. Because these ligands were sequenced using a primer that annealed adjacent to the 35N region, often the sequence of the first few nucleotides at the 3' end was indecipherable. As the sequences of the unreadable regions are not necessary for this analysis, they are represented by "N"s.

FIGS. 4A and 4B show sequences isolated from the library after cycle 15 (SEQ ID NOS:45–72). The top of the Figure shows the upstream PCR primer (see FIG. 1B) and the complement of the downstream PCR primer and downstream cloning primer (see FIG. 1B). Only the 35 positions originally randomized are shown below for each numbered individual. However, the full-length sequence includes the upstream and downstream sequences as shown at the top of the Figure. Isolates were grouped and aligned by common primary sequence elements. Clones are indicated by number. Isolates were grouped and aligned by common elements. CCCCT, or a variant of this pentamer, is shown as boxed. Other regions of similarity among isolates are shaded.

Figures 5A, 5B:
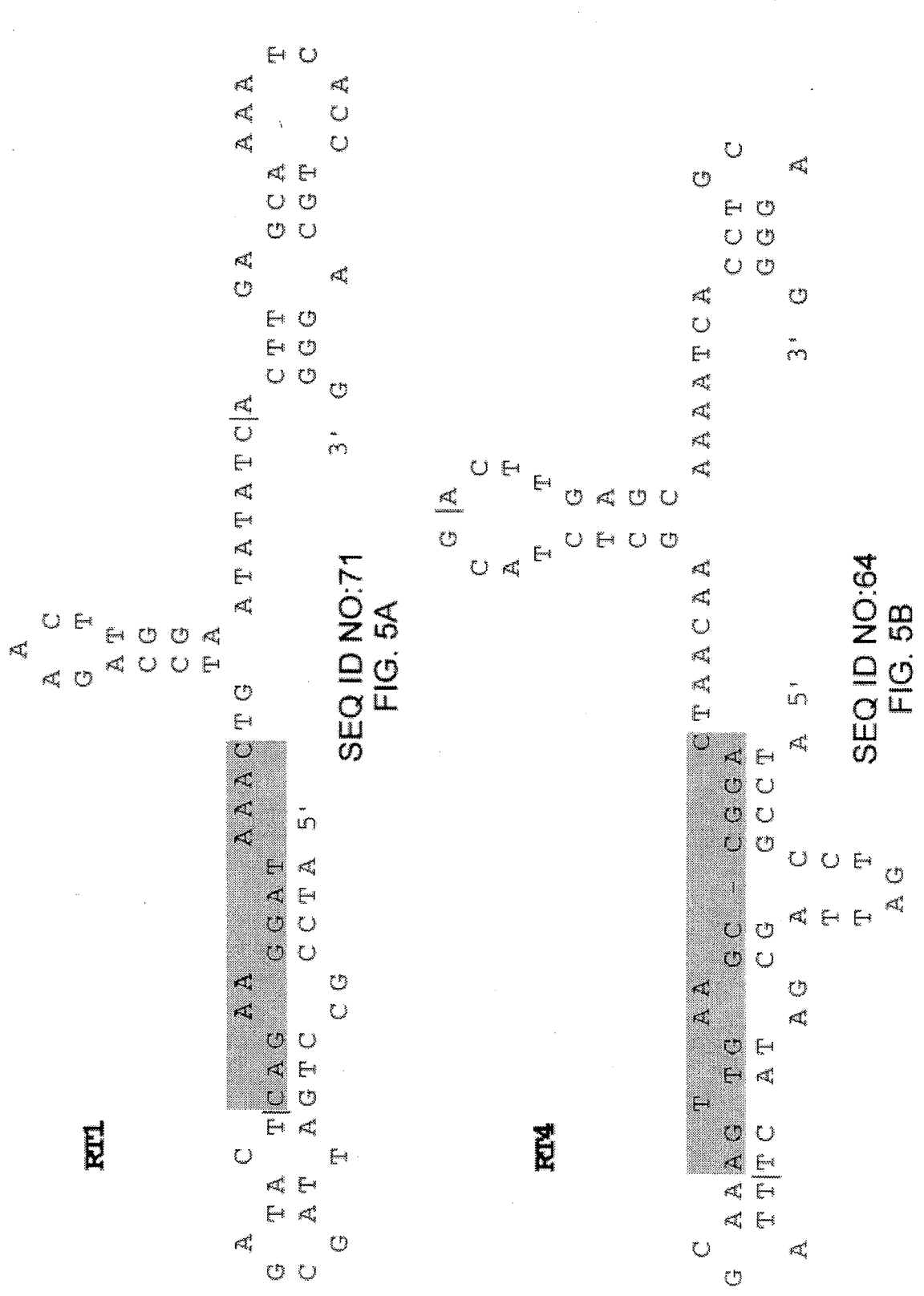
Figures 5D, 5F:
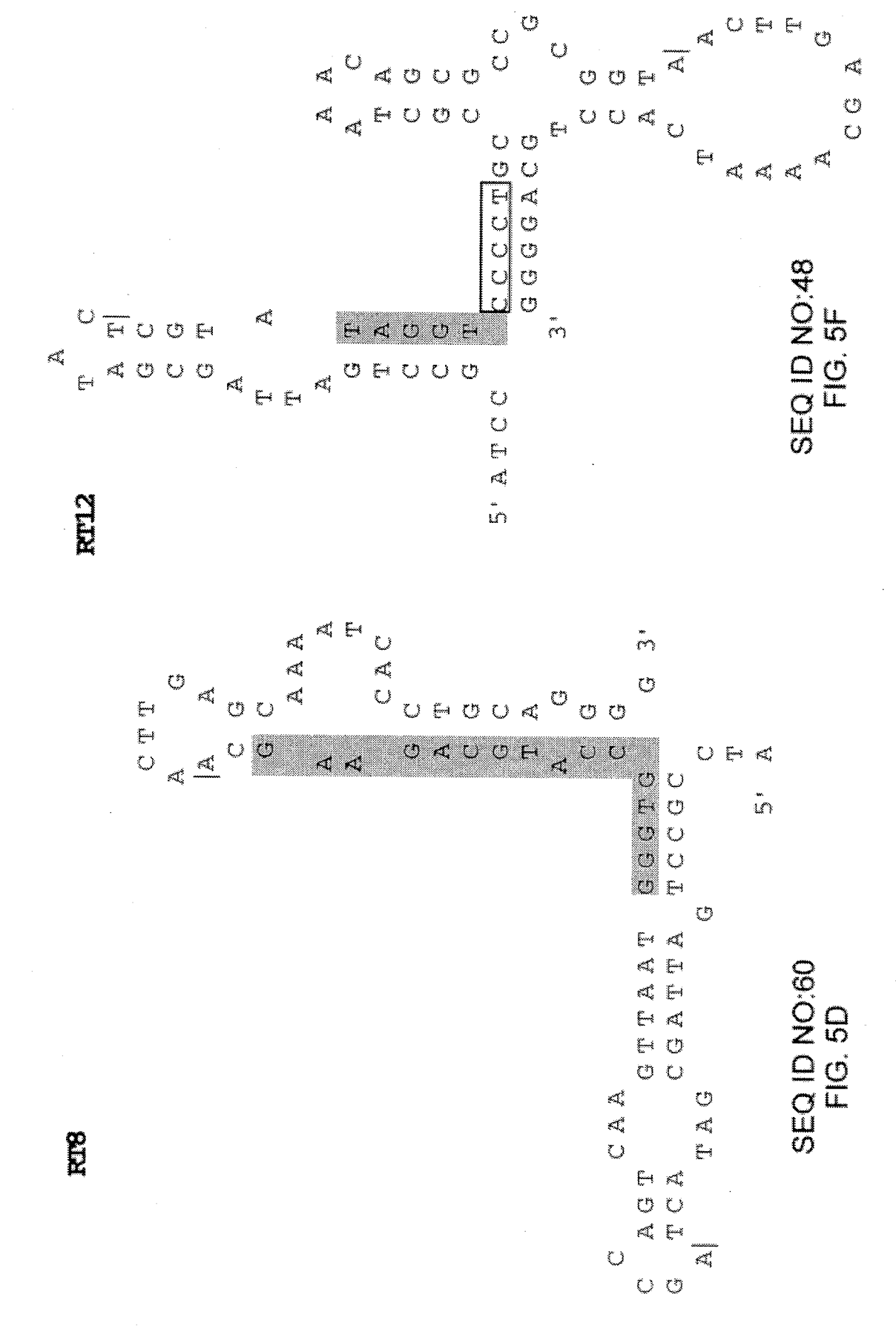
Figures 5G, 5H:
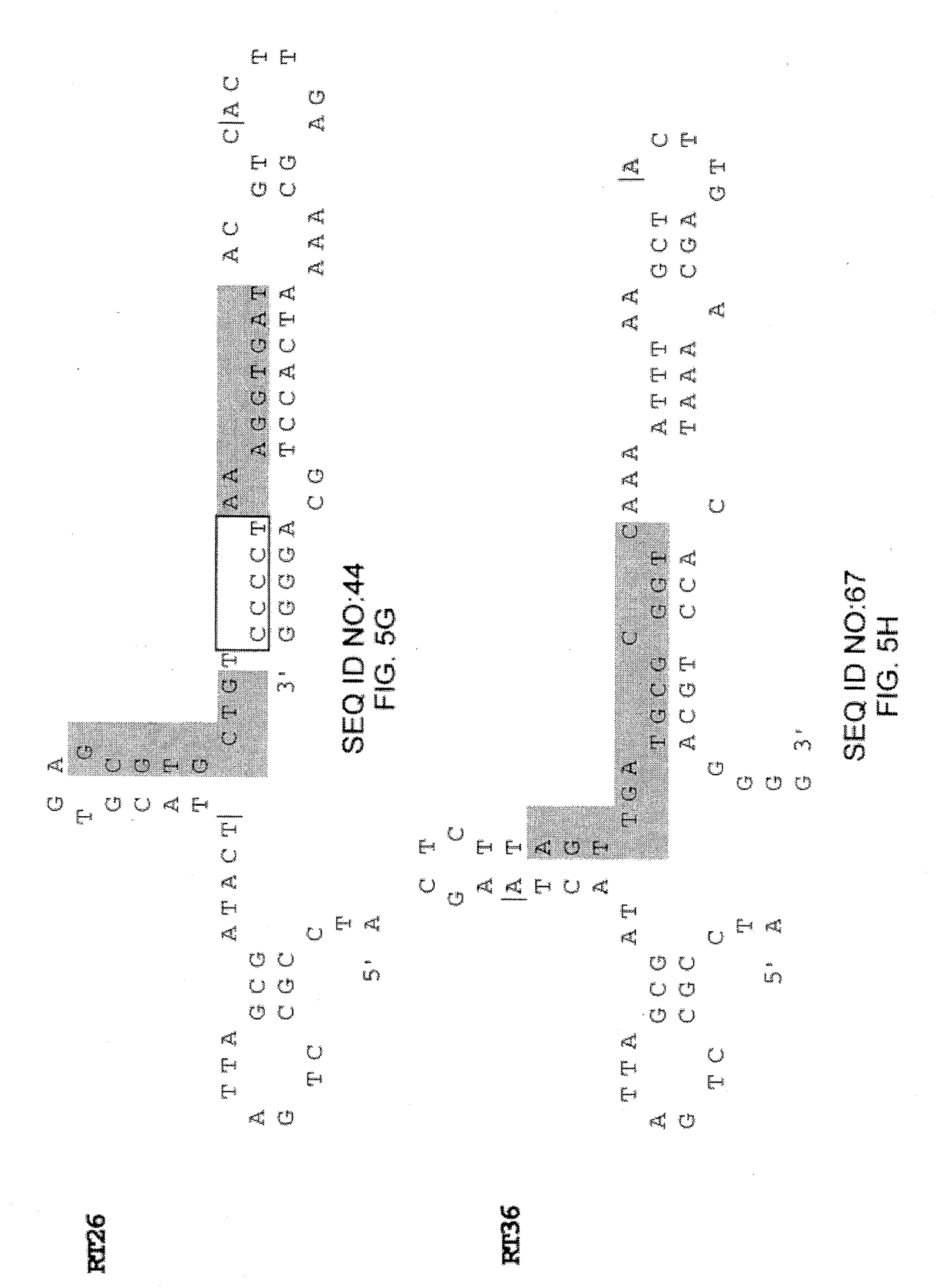

FIGS. 5A–5H show the predicted secondary structures of eight individual ligands (RT1 (SEQ ID NO:71), RT4 (SEQ ID NO:64), RT6 (SEQ ID NO:57), RT8 (SEQ ID NO:60), RT10 (SEQ ID NO:56), RT12 (SEQ ID NO:48), RT26 (SEQ ID NO:44), and RT36 (SEQ ID NO:67)). The structure of each of the eight ligands in this figure include elements common to many other members of its respective group (boxed or shaded as in FIG. 4). The 35 positions originally randomized are demarcated by vertical lines.

FIGS. 6A–6E show the conserved internal loop motif. The sequence and predicted secondary structure of the internal loop motif of ligands RT26 (SEQ ID NO:44) and RT1 (SEQ ID NO:71) is illustrated, along with variants of the motif found in ligands RT4 (SEQ ID NO:64), RT8 (SEQ ID NO:60), and RT36 (SEQ ID NO:67). The conserved loop sequences are indicated in boldface. The stems closing each side of the internal loop vary in both sequence and length.

FIGS. 10A–10I show the inhibition of RNA-dependent DNA polymerase activity of HIV-1 RT. The substrate for the inhibition assay is shown in FIG. 10A. Extension reaction products are shown for R0 (degenerate ssDNA library), RNApk (RNA pseudoknot), RT1 (SEQ ID NO:71), and RT26 (SEQ ID NO:44) in FIGS. 10B, D, F and H. The $K_i'$ plots are also shown in FIGS. 10C, E, G, and I.

FIGS. 11A and 11B show the sequences of individuals isolated from the biased randomization SELEX of RT1 (SEQ ID NOS:76–91). The 35N positions, aligned with the "wild-type" sequence of RT1 are shown in FIG. 11A. Positions absolutely conserved are indicated with an open circle, those partially conserved (fewer than three individuals possess a substitution) with a triangle, and those preferring a substitution with a bullet. Complementary sequences able to form secondary structure interactions are underlined. Predicted secondary structure of RT1 with a consensus sequence (suggested by the results of A) replacing the "wild-type" 35N region is shown in FIG. 11B (SEQ ID NO:92). Only the upstream invariant region and 35N region are shown. Variable positions are represented with an N. The two preferred substitutions ($G_2$ and $T_{18}$) are indicated in boldface.

FIGS. 12A–12C show the predicted secondary structures of RT1 (SEQ ID NO:71) and truncates.

DETAILED DESCRIPTION OF THE INVENTION

Figure 1A:
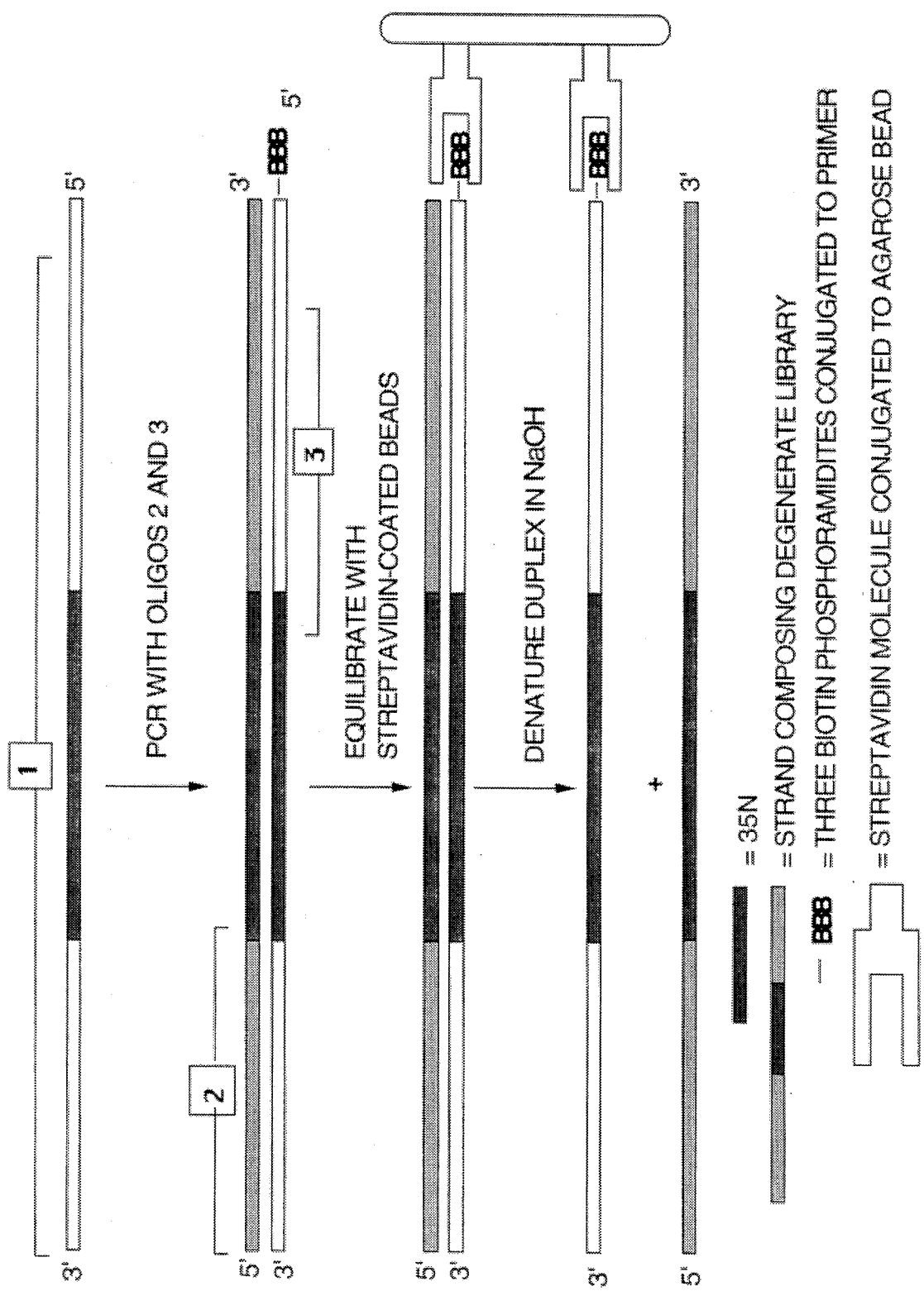

This application describes high-affinity DNA ligands to HIV-1 RT identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, U.S. patent application Ser. No.

07/931,473, filed Aug. 17, 1992, entitled Nucleic Acid Ligands, now U.S. Pat. No. 5,270,163 (see also PCT/US91/04078). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate an enriched candidate mixture. The SELEX Patent Applications also describe ligand solutions obtained to a number of target species, including both protein targets where the protein is and is not a nucleic acid binding protein.

SELEX provides high affinity ligands of a target molecule. This represents a singular achievement that is unprecedented in the field of nucleic acids research. The present invention applies the SELEX procedure to the specific target of HIV-1 reverse transcriptase (RT). In the Example section below, the experimental parameters used to isolate and identify the nucleic acid ligands to HIV-1 RT are described.

In order to produce nucleic acids desirable for use as a pharmaceutical, it is preferred that the nucleic acid ligand 1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In co-pending and commonly assigned U.S. patent application Ser. No. 07/964,624, filed Oct. 21, 1992 ('624), methods are described for obtaining improved nucleic acid ligands after SELEX has been performed. The '624 application, entitled Methods of Producing Nucleic Acid Ligands, is specifically incorporated herein by reference.

In the present invention, a SELEX experiment was performed in search of single-stranded DNA ligands with specific high affinity for HIV-1 RT from a degenerate library containing 35 random positions (35N). A large family was identified with an apparent affinity for HIV-1 RT about 700 times higher than the library from which they originated (described in Examples 1 and 2, infra). At least seven members of this diverse family, sharing little similarity with each other or with the RNA pseudoknot at the levels of primary and secondary structure, inhibit the RNA-dependent DNA polymerase activity of HIV-1 RT at very low concentrations, possibly competing with substrate for the polymerase active site by virtue of their higher affinity for RT (described in Example 2, infra). For at least one inhibitor this inhibition is specific for HIV-1 RT, as the polymerase activity of reverse transcriptases from Avian Myeloblastoma Virus (AMV-RT) and Moloney Murine Leukemia Virus (MMLV-RT) were unaffected by the presence of the inhibitory DNA ligand RT1t49 (SEQ ID NO:93). For one of the ssDNA inhibitors (RT1) (SEQ ID NO:71), the importance of each selected residue was assessed by introducing an average of 9 new mutations (in the originally randomized region) and selecting for variants maintaining high affinity (described in Example 4, infra). Based on these results, we then removed 40% of the ligand and observed only a moderate loss of affinity. The 5' half of the truncate contained an internal loop motif common to other members of the selected library, likely creating a helix bend that provides a specific shape for direct contact by HIV-1 RT. The truncated ligand inhibited the polymerase activity of HIV-1 RT as well as the full-length ligand (see Example 4, infra), and binding of the truncate and the RNA pseudoknot were mutually exclusive (see Example 5, infra), suggesting they interact with HIV-1 RT at a common site.

Figure 3B:
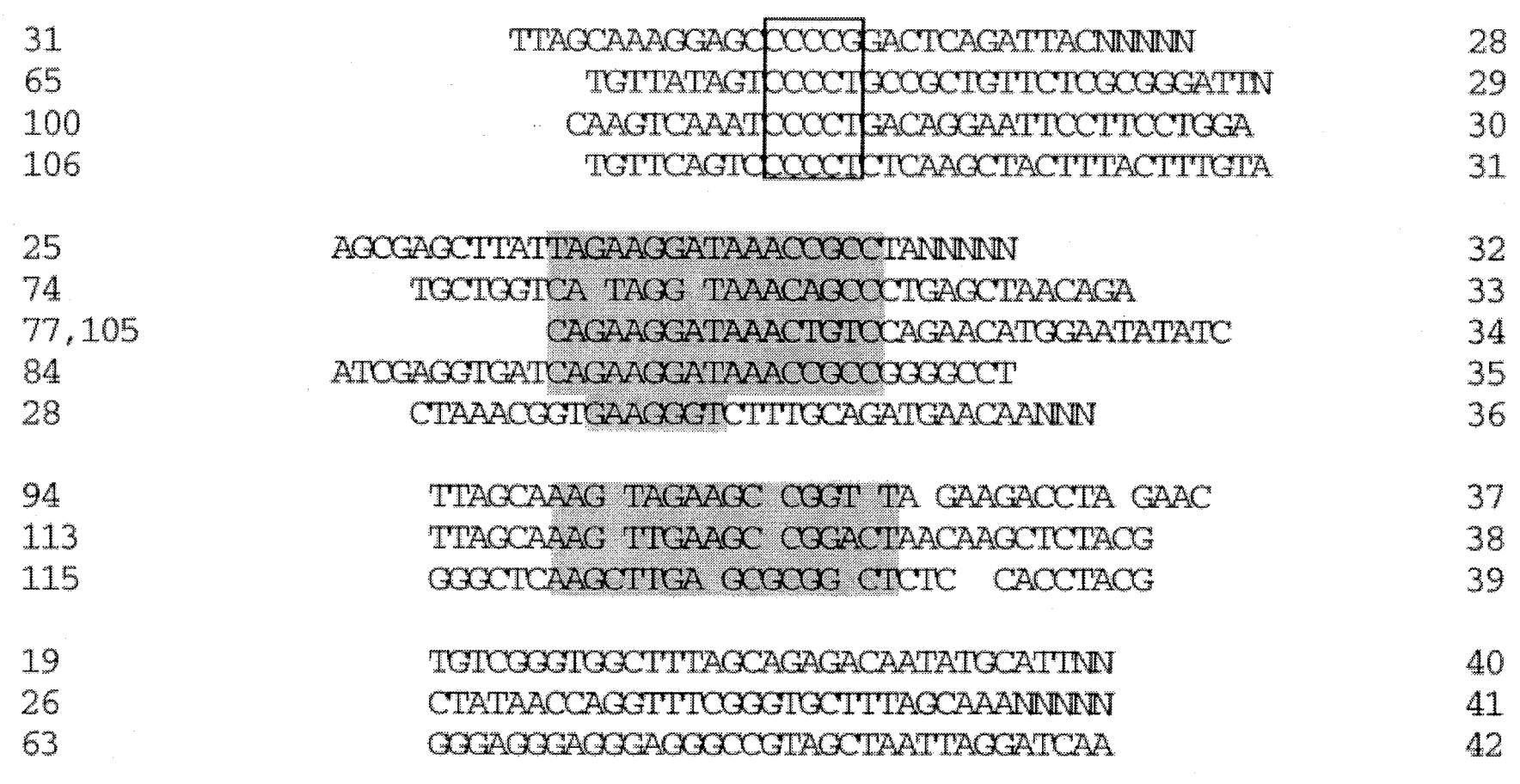
Figure 4A:
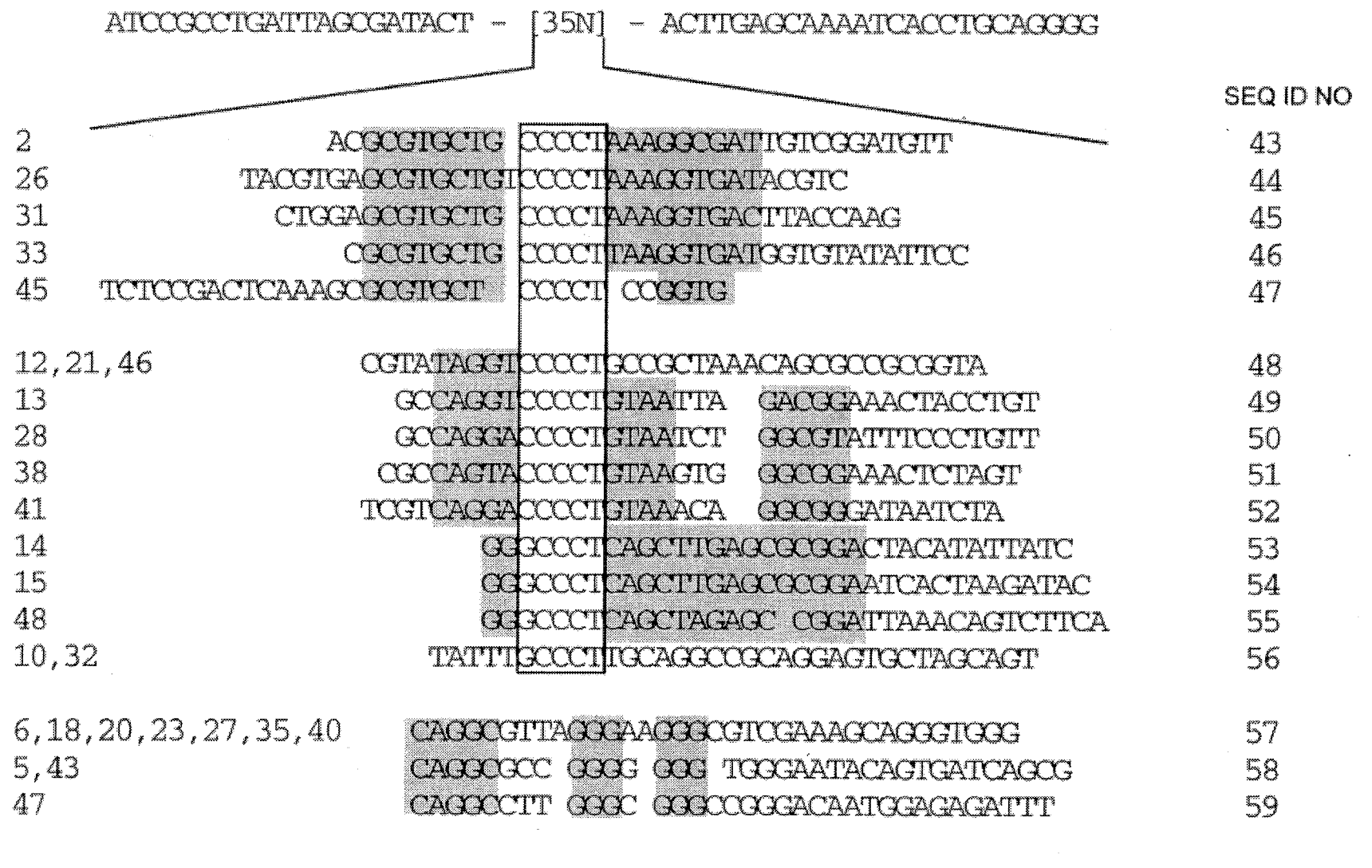

This invention includes the specific DNA ligands to HIV-1 RT shown in FIG. 3 (SEQ ID NOS:6–42), identified by the method described in Example 1. This invention also includes the specific DNA ligands to HIV-1 RT shown in FIG. 4 (SEQ ID NOS:43–72), as identified by the method described in Example 1. This invention further includes ssDNA ligands of HIV-1 RT that are inhibitors of HIV-1 RT. The scope of the ligands covered by this invention extends to all DNA ligands of HIV-1 RT, modified and unmodified, identified according to the SELEX procedure. More specifically, this invention includes nucleic acid sequences that are substantially homologous to the DNA ligands shown in FIGS. 3 and 4. By substantially homologous it is meant a degree of primary sequence homology in excess of 70%, most preferably in excess of 80%. A review of the sequence homologies of the DNA ligands of HIV-1 RT shown in FIGS. 3 and 4 shows that sequences with little or no primary homology may have substantially the same ability to bind HIV-1 RT. For these reasons, this invention also includes DNA ligands that have substantially the same three-dimensional structure as the ligands presented herein and substantially the same ability to bind HIV-1 RT as the nucleic acid ligands shown in FIGS. 3 and 4. Substantially the same ability to bind HIV-1 RT means that the affinity is within one to two orders of magnitude of the affinity of the ligands described herein. It is well within the skill of those of ordinary skill in the art to determine whether a given sequence— substantially homologous to those specifically described herein—has substantially the same ability to bind HIV-1 RT.

This invention also includes the ligands as described above, wherein certain chemical modifications are made in order to increase the in vivo stability of the ligand or to enhance or mediate the delivery of the ligand. Modifications include chemical substitutions at the deoxyribose and/or phosphate and/or base positions of a given DNA sequence. For example, modifications at the 2' position of the sugar (e.g., replacement of a H at the 2' position with a chloro, fluoro, or O-methyl) may provide resistance to intracellular or extracellular endonucleases. Additionally, a 3' cap consisting of three nucleotides that are connected with phosphodithioate bonds could provide resistance for DNA ligands against 3'-5' exonucleases. Such modifications may be made post-SELEX (modification of previously identified unmodified ligands) or by incorporation into the SELEX process.

The DNA ligands to the HIV-1 RT protein described herein are useful as pharmaceuticals and as part of gene therapy treatments. According to methods known to those skilled in the art, the nucleic acid ligands may be introduced intracellularly into cells infected with the HIV virus, where the nucleic acid ligand will compete with the substrate for the nucleic acid binding site and/or polymerase active site. As such, transcription of HIV genes can be prevented.

The invention also includes the ligands as described above, wherein nucleotide analogs are incorporated at a specific position, and further that these nucleotide analogs possess a reactive group which is able to covalently crosslink the ligand to HIV-1 RT upon binding. This invention also includes the ligands as described above, wherein covalent crosslinking is coupled to the activity of the HIV-1 RT.

The following examples are provided to explain and illustrate the present invention and are not to be taken as limiting of the invention. Example 1 describes the experimental procedures used to generate high-affinity ssDNA ligands to HIV-1 RT. Example 2 describes the high-affinity DNA ligands to HIV-1 RT shown in FIGS. 3 and 4. Example 3 describes suicide inhibitors of HIV-1 RT. Example 4 describes the essential elements of RT1. Example 5 describes the competition between RT1 and RNA Pseudoknot for RT binding.

EXAMPLE 1

Experimental Procedures

Materials.

Recombinant HIV-1 RT overexpressed in *E. coli* cells was purified according to the procedure described in Davies, J. F. et al. (1991) Science 252:88–95. Enzyme was aliquoted and stored at −70° C. in HRT Buffer (200 mM KOAc, 50 mM Tris-Acetate, pH 7.4, 6 mM MgCl$_2$, 10 mM DTT). Aliquots thawed and refrozen more than once were discarded. All other materials were purchased from commercial sources.

Generation of Degenerate ssDNA Library.

A population of synthetic DNA oligonucleotides (oligo 1) (SEQ ID NO:1) containing 35 random nucleotides flanked by invariant primer annealing sites was amplified by the Polymerase Chain Reaction (PCR) using oligos 2 (SEQ ID NO:2) and 3 (SEQ ID NO:3) as primers (FIG. 1). Oligo 3 (SEQ ID NO:3) had three biotin phosphoramidites covalently attached to its 5' terminus during synthesis. The 81 nucleotide double-stranded PCR product was size-purified on a 12% non-denaturing acrylamide gel and 100–300 pmol were applied to 100 µl of a Pierce streptavidinagarose bead matrix suspended in Buffer A (50 mM NaCl, 10 mM Tris-HCl, pH 7.5, 1 mM EDTA). After equilibration for 30 minutes at 20° C. to allow the biotinylated double-stranded DNA (dsDNA) to bind the streptavidin beads, unbound dsDNA was removed with five 500 µl washes of Buffer A, and the matrix-bound dsDNA was denatured in 400 µl of 0.15N NaOH for 15 minutes at 37° C. As these conditions were not harsh enough to disrupt the biotinstreptavidin interaction, denaturation released only the non-biotinylated DNA strand from the bead complex. The free DNA was collected and precipitated, yielding 70–200 pmol of single-stranded DNA (ssDNA). 10–20 pmol were $^{32}$P labeled at the 5' end with T4 Polynucleotide Kinase and the product was size-purified on an 8% denaturing acrylamide gel and combined with the remaining (unlabeled) ssDNA to comprise the degenerate ssDNA library used for the selections.

Nitrocellulose Filter Binding Assays.

Oligonucleotides bound to proteins can be effectively separated from the unbound species by filtration through nitrocellulose membrane filters (Yarus, M. and Berg, P. (1970) Anal. Biochem. 35:450–465; Lowary, P. T. and Uhlenbeck, O. C. (1987) Nucleic Acids Res. 15:10483–10493; Tuerk, C. and Gold, L. (1990) Science 249:505–510). The affinity of the random ssDNA library for HIV-1 RT was determined using a protein excess nitrocellulose filter binding assay as described in Carey, J. et al. (1983) Biochemistry 22:2601–2609. Selections were performed with a saturating ssDNA concentration to promote competition among DNA ligands for a limited number of available target binding sites. The percent of target-dependent DNA retention was minimized for each selection to ensure maximum enrichment of the library for target binders; however, to avoid propagation of members with high affinity for nitrocellulose, selections were repeated if target-free (background) retention was greater than 10% of target-dependent retention.

For the first selection, 500 nM HIV-1 RT and 2 µM ssDNA (100 pmol or about $10^{14}$ different molecules) were equilibrated at 37° C. for 5 minutes in HRT Buffer and filtered through nitrocellulose to sequester target-bound ligands. Target-free selections were done in duplicate to measure and correct for background binding levels. The fraction of total DNA retained by the filters was calculated by measuring radiation without fluor in a scintillation counter. Ligands were harvested from the filter as described in Tuerk, C. and Gold, L. (1990) Science 249:505–510, amplified by PCR, denatured from the biotinylated complementary strand, and end-labeled as described above to regenerate the library. The affinity of the pool for HIV-1 RT was measured prior to selections 6, 8, 10 and 12, and was estimated for the remaining selections. These values determined the ligand concentration necessary for saturation each selection. As the affinity of the population for HIV-1 RT increased, the concentrations of ligand and RT were reduced accordingly to increase selection stringency.

Equilibrium Dissociation Constants.

In the simplest case, equilibrium binding of ssDNA ligand (L) to HIV-1 RT protein (P) can be described by equation (1):

$$PL \underset{}{\overset{K_d}{\rightleftharpoons}} P_f + L_f \qquad (1)$$

where $K_d=([P_f][L_f]/[PL])$ is the equilibrium dissociation constant between the protein and ssDNA ligand, $P_f$ is free protein, $L_f$ is free ligand, and PL is protein-ligand complex.

Using the mass balance equations, the fraction of bound ligand at equilibrium (q) can be expressed in terms of measurable quantities according to equation (2):

$$q=(P_t+L_t+K_d-((P_t+L_t+K_d)^2-4P_t L_t)^{1/2}) \quad (2)$$

where $P_t$ and $L_t$ are total protein and ligand concentrations.

For competition experiments an additional equilibrium exists between the protein (P) and competitor (C) as described by equation (3):

$$PC \underset{}{\overset{K_c}{\rightleftharpoons}} P_f + C_f \quad (3)$$

where $K_c=([P_f][C_f]/[PC])$ is the equilibrium dissociation constant between the protein and competitor, $P_f$ is free protein, $C_f$ is free competitor, and PC is protein-competitor complex. Competition titration experiments were analyzed using equation (4) to determine the concentration of free protein as a function of the total competitor concentration:

$$[P_t]=[P_f](1+K_d[L_t]/(1+K_d[P_f])+K_c[\ C_t]/(1+K_c[P_f])) \quad (4)$$

This equation assumes a 1:1 binding stoichiometry for both reactions and that only one species is bound to protein at a time. Since it is difficult to obtain a direct solution for this equation in terms of $[P_f]$, we have utilized iteration to determine values of $[P_f]$ to a precision of $1\times10^{-15}$. To utilize this equation to follow [PL] as a function of competitor added, we also need the following expression:

$$[PL]=K_d[P_f]([L_t]/(1+K_d[P_f])) \quad (5)$$

These equations were used in the non-linear least-squares data analysis to obtain the best fit parameters for $K_c$ as a function of $[C_t]$ for each competition experiment. The value used for $K_d$ for this fitting analysis was the mean experimental value determined with equation (2) in the absence of competitor.

Inhibition titration experiments were also analyzed using equations (4) and (5), with the primer:template junction substrate as the ligand (L) and the ssDNA ligand the competitor (C). Inhibition values are reported as $K_i'$ rather than $K_i$ (traditionally measured using a Michaelis-Menten analysis comparing reaction rates as a function of substrate concentration) because their mode of inhibition is likely a binding competition between substrate and ssDNA ligand, more accurately described by a $K_c$ value as illustrated above.

Cloning and Sequencing Isolates.

Following round 15, one pmol of the library was amplified by PCR using oligo 3 (SEQ ID NO:3) without the biotins (containing a Pst I restriction endonuclease cleavage site) and oligo 4 (SEQ ID NO:4) (containing a Bam HI site) as primers (see FIG. 1). Double-stranded products were digested with Pst I and Bam HI and subsequently ligated into pUC19, similarly digested prior to the ligation. The vectors were electroporated into E. coli DH1α cells and oligo 5 (SEQ ID NO:5), complementary to 16 nucleotides of the PUC19 polylinker region, was used as a primer for dideoxy sequencing of the cloned inserts. These techniques are well-known in the art. A detailed description of these techniques can be found in Schneider, D. et al. (1993) FASEB 7:201–207. Large quantities of individual DNA ligands were prepared by amplifying the vector inserts by PCR using oligos 2 (SEQ ID NO:2) and 3 (SEQ ID NO:3) as primers and following the streptavidin matrix purification technique described above to isolate ssDNA.

Assay For Inhibition of RNA-Dependent DNA Polymerase Activity.

A substrate for the RNA-dependent DNA polymerase activity of HIV-1 RT was assembled by annealing an 18 nucleotide, 5' end-labeled DNA primer to a 30 nucleotide RNA template with a complementary 3' end (see FIG. 10), and purifying the duplex on a 12% non-denaturing acrylamide gel. The primer sequence matched the 3' terminal 18 nucleotides of tRNA$^{Lys,3}$, responsible for priming minus-strand DNA synthesis of the HIV-1 genome, and the template sequence paralleled the HIV-1 genomic primer binding site and downstream 12 nucleotides. A dilution series of inhibitory ssDNA ligand (to give a final concentration of 0, 1, 3, 9, 27, or 81 nM) was denatured in HRT Buffer at 70° C. for 5 minutes and allowed to renature slowly at 20° C. The primer:template substrate was added to a final concentration of 40 nM, along with dNTP's at 400 µM. The 10 µl reaction was initiated with the addition of either HIV-1, AMV, or MMLV-RT (to give a final concentration of 10 nM), allowed to proceed for 5 minutes at 37° C., and terminated with one volume of formamide. Extension products were separated on an 8% denaturing acrylamide gel and quantitated with an Ambis radioanalytic imager.

Intramolecular Extension Assay.

In a 10 µl reaction, 0.1 pmol of 5' end-labeled ssDNA ligand was denatured and slowly renatured as above and combined with 400 µM dNTP's and a saturating concentration of enzyme (200 nM HIV-1 RT, 100 nM AMV RT, or 0.6 units/ml Sequenase T7 DNA polymerase, all shown to have equivalent activity), extended for 30 minutes at 37° C., and terminated with one volume of formamide. To determine the precise location of the annealed 3' end, extensions were also done with Sequenase in the presence of 25 µM ddATP. Extension products were separated on an 8% denaturing acrylamide gel.

Biased Randomization Selections.

A library of ligand RT1 variants was chemically synthesized, incorporating the "wild-type" nucleotide at a frequency of 0.625 and each of the "mutant" nucleotides at a frequency of 0.125 in the 35N cassette. Selections for HIV-1 RT affinity were performed as described above; however, a simpler protocol was used to isolate and label the non-biotinylated DNA strand. During the amplification step, α-$^{32}$P dATP was incorporated into both strands of the duplex. The strands were separated on an 8% denaturing acrylamide gel by virtue of the retarded migration of the strand possessing the three biotins, and the non-biotinylated strand was recovered. Because the ssDNA was internally-labeled, end-labeling was not necessary and the recovered sample was ready for the next selection round.

EXAMPLE 2

DNA Ligands to HIV-1 RT

Selected ssDNA Ligands Bind 700 Times Better After 15 SELEX Cycles.

Figure 2:
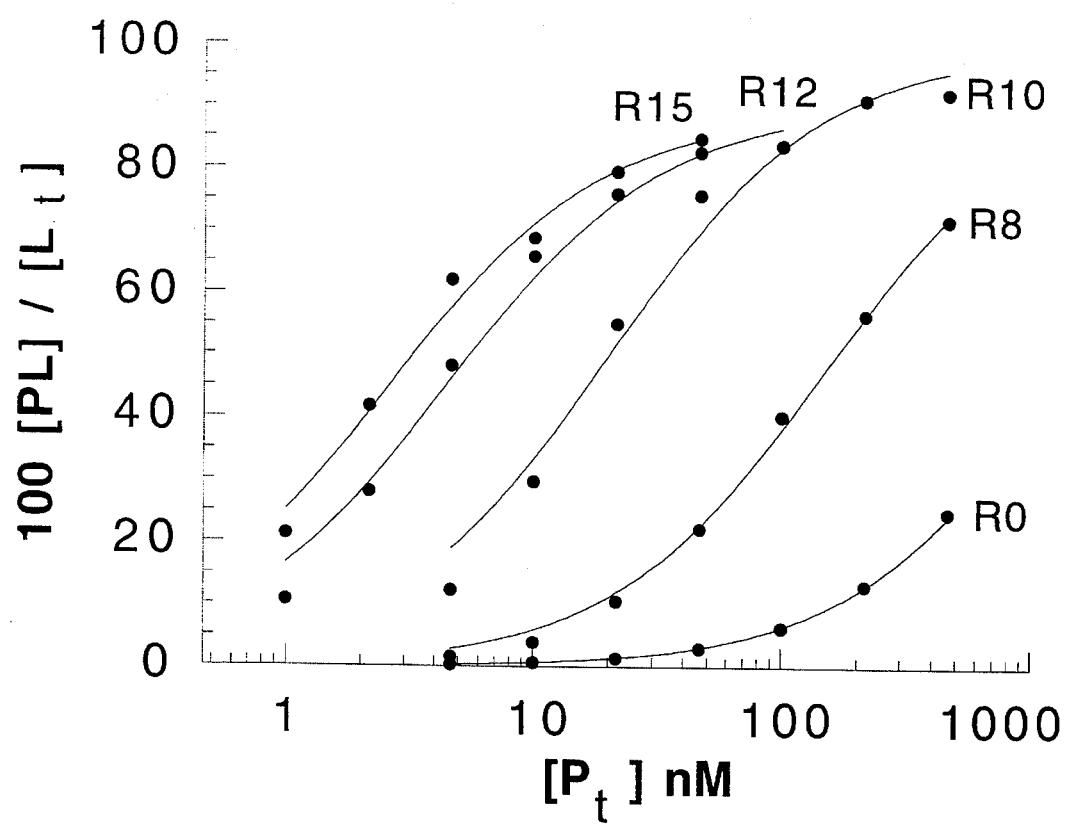
FIG. 2 shows protein excess binding curves measuring affinity of ssDNA library after various SELEX cycles. $K_d$ values were determined using an algorithm to fit the data points to Equation 2 of Example 1.

Following the selection guidelines described in Example 1, we were able to enrich the DNA library for RT binders from an initial apparent $K_d$ value of 1400 nM to a final value of 4 nM in 12 cycles (see FIG. 2). Enrichment began slowly, requiring 8 cycles to improve the affinity by one log (the apparent $K_d$ of the round 8 library was 150 nM), but increased quickly in the later cycles as predicted by Irvine, D. et al. (1991) J. Mol. Biol. 222:739–761, with the affinity improving another 10-fold by round 10 ($K_d$ equal to 10 nM), and an additional 3-fold by round 12 ($K_d$ equal to 4 nM).

Forty different individuals were isolated after 12 cycles (FIG. 3) (SEQ ID NOS:6–42). Of the 40 different individuals isolated after 12 cycles, 3 of every 4 contained the pentamer CCCCT (or a variation of this pentamer) in the central 35 nucleotide cassette (FIG. 3). The sequence of the invariant 3' end of each molecule in the library was AGGGG, and when paired to the internal CCCCT, the resulting duplex mimicked a primer:template junction substrate recognized naturally by the enzyme. A more careful analysis revealed additional base pairing: 13 of the 40 paired at least 6 nucleotides, 9 paired at least 7, 3 paired at least 8, and 1 contained the sequence CCCCTGTAG pairing with the 3' terminal CTGCAGGGG at 9 positions. If we assembled a collection of 40 randomly-chosen individuals from the degenerate library, the expected distribution of individuals able to form a duplex with the 3' terminus would be: 20 pairing 5 nucleotides, 4 pairing 6, 2 pairing 7, 1 pairing 8, and 0 pairing 9 (see infra). This overrepresentation of junctions in the degenerate library suggested additional components were required for high affinity binding.

Our decision to isolate and sequence individual members of the enriched library after 12 SELEX cycles was made based on the enrichment profile shown in FIG. 2, where the small affinity change seen between selections ten and twelve suggested sufficient enrichment had occurred. Upon examination of the sequences, two observations were made that led us to believe that further rounds were necessary. First, of the 37 individuals isolated from the enriched library, only three were represented more than once, and none was represented more than two times. Sequence redundancy is often an indicator of sufficient enrichment, as highly represented sequences are believed to possess a component conferring a selectable advantage, ultimately resulting in their enrichment to a significant fraction of the selected library. Second, the majority of molecules selected by HIV-1 RT had the potential to form structures mimicking primer:template junctions. At first, the preference for junctions was discouraging as we hoped to identify ligands with complex, interesting secondary structures, but an analysis of sequence representation (discussed infra) suggested that complex ligands did exist in the degenerate library and might be found with a few more selection cycles.

While most of the selected ligands had the potential to form a primer:template junction, the sequences forming the duplex varied widely among individuals, most often forming imperfect helices with no apparent similarities. Because the frequency of individuals in the degenerate library with this characteristic was very high, specific binding to HIV-1 RT had to depend on more than the presence of a junction. If we accept G:T annealing as a stable base-pair, one of every 2 molecules in the degenerate library possessed a 5 base-pair junction. (This number was derived by calculating the fraction of pentamers with the sequence C/T-C/T-C/T-C/T-T, 1 in 64, multiplying by 31 to account for the number of windows a 35N region provides for a pentamer.) Similar calculations reveal that 1 in 630 individuals in the degenerate library could form a 10 base-pair junction, 1 in $4 \times 10^5$ a 15 base-pair junction, and 1 in $2.7 \times 10^8$ a 20 base-pair junction. The distribution of junction lengths of the round 12 library was unimpressive knowing that approximately 70% of the degenerate library consisted of ligands containing perfect junctions 5 base-pairs long or greater. Clearly, more complex ligands with higher affinity existed in the degenerate library, but were severely outnumbered by the remarkably high representation of individuals (with reasonable affinity for HIV-1 RT) containing a primer:template junction. The tremendous competition for available target binding sites increased the number of cycles necessary to enrich the higher affinity individuals to a sufficient fraction of the population, as predicted by Irvine, D. C., Tuerk, C., and Gold, L. (1991) J. Mol. Bio. 222:739–76.

We performed three more cycles to enrich for molecules possessing binding features in addition to (or instead of) the stable primer:template junction. Individuals isolated from this round 15 library are herein referred to as RT "N," where "N" represents the ligand number corresponding to the sequences shown in FIG. 4 (SEQ ID NOS:43–72). Only after three additional SELEX cycles did the underrepresented, but structurally more complex individuals surpass those lower affinity members possessing junctions. The majority of individuals in the round 15 library were unable to form primer:template junctions with the 3' terminus, but did have the potential to form ordered structures, primarily long helices with specific interruptions. Individuals able to form junctions that survived the three extra cycles each had additional components that increased their affinity relative to the round 12 library. Of the 30 different individuals isolated from the final population, only 1 of every 3 mimicked a primer:template junction, and those that did shared additional regions of similarity; for example, one subset had in common the octamer GCGTGCTG immediately upstream, and the nonomer AAAGGTGAT immediately downstream of the CCCCT pentamer (FIG. 4). Replacement of the conserved upstream octamer with (dA)8 resulted in a ligand with an affinity for HIV-1 RT as poor as the degenerate library (data not shown).

Compared with the isolates of the round 12 library, more members of the round 15 library were multiply represented (RT6 (SEQ ID NO:57) was represented 7 times, RT8 (SEQ ID NO:60) 4 times, RT12 (SEQ ID NO:48) 3 times, etc.), indicating a more highly enriched representation of HIV-1 RT binders existed after 15 cycles. The high number of redundant sequences and conserved elements in the round 15 library indicated that further enrichment was unnecessary. The three additional cycles resulted in a decrease in the apparent $K_d$ of the library to 2 nM, a total increase in affinity of 700-fold over the degenerate library. The isolates from this library were classified into subsets with common sequence elements. At least one from each subset (for a total of 8) was chosen for further characterization.

HIV-1 RT Binders Characterized by Long Interrupted Helices.

The primary sequence diversity between subsets suggested that if there was a common element responsible for the affinity, it existed at a higher level of structure. Unfortunately, a reliable set of rules characterizing the folding of ssDNA molecules has not been elucidated, restricting us to use of the best tool available, an algorithm that uses rules for RNA folding to predict secondary structure (Jaeger, J. A. et al. (1989) Proc. Natl. Acad. Sci., U.S.A. 86:7706–7710; Zuker, M. (1989) Science 244:48–52). Potential structures offered by this algorithm for each of the eight ssDNA ligands are illustrated in FIGS. 5A–H. Optimal and suboptimal structures were compared within each group, and conserved structural elements were used to predict functional binding motifs. All of the ligands have the potential to form structures characterized by a high degree of base pairing, often making extensive use of the invariant regions to form long helices interrupted by mismatches, bulges, and internal loops. Ligands RT10 (SEQ ID NO:56), RT12 (SEQ ID NO:48), and RT26 (SEQ ID NO:44) are able to pair their 3' terminal AGGGG with an internal CCCCT to form an intramolecular primer:template junction. Of particular interest is the helix of RT26 (SEQ ID NO:44), containing a potential internal loop with an AA opposite a CG as shown in FIG. 6A. This motif can also be formed in ligand RT1 (SEQ ID NO:71), as well as variants in ligands RT4 (SEQ ID NO:64) (an AA opposite an AG), RT8 (SEQ ID NO:60)

(a CAA opposite a TAG), and RT36 (SEQ ID NO:67) (an AA opposite an A) (FIGS. 6B–E).

Binding Curves Confirm High Affinity of Individual Ligands.

Figure 7A:
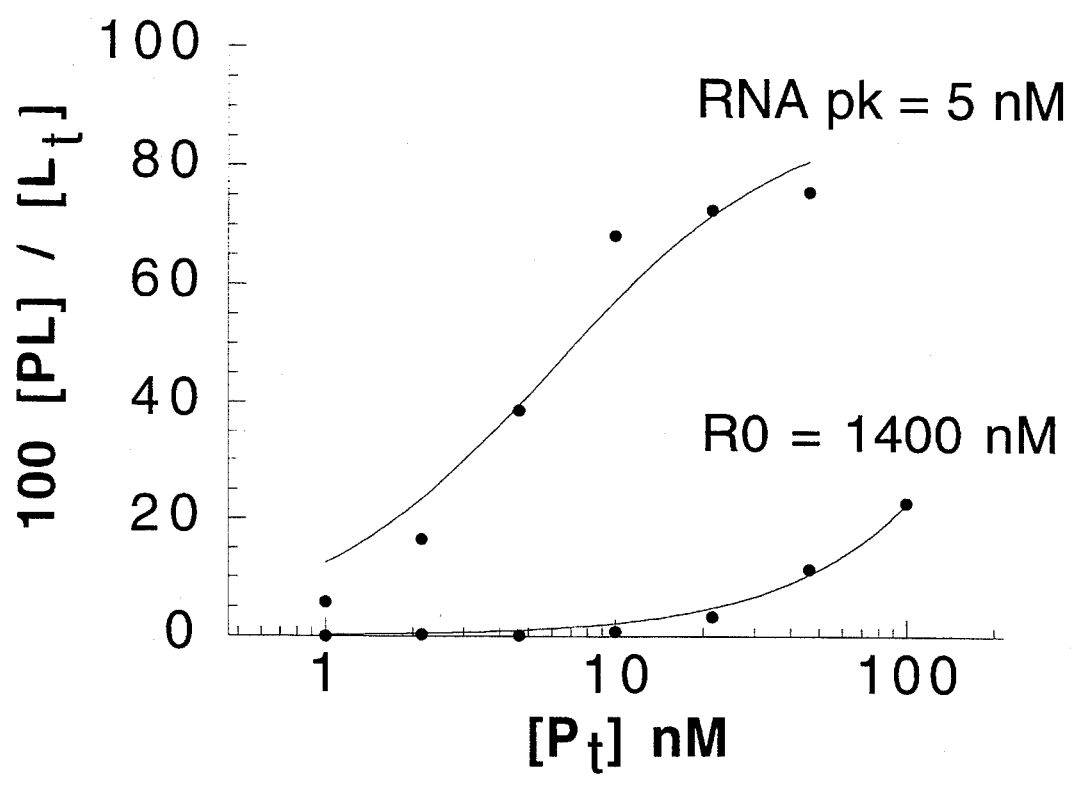
FIGS. 7A–7C show the protein excess binding curves of selected individuals. The percent of ligand bound is plotted as a function of total protein concentration. The dissociation constants of the RNA pseudoknot (RNA pk) and the degenerate library (R0) are shown in FIG. 7A. The dissociation constants of RT1 (SEQ ID NO:71), RT4 (SEQ ID NO:64), RT6 (SEQ ID NO:57), RT8 (SEQ ID NO:60), RT10 (SEQ ID NO:56), RT12 (SEQ ID NO:48), RT26 (SEQ ID NO:44), and RT36 (SEQ ID NO:67) are shown in FIGS. 7B and 7C. Dissociation constants were determined as in Example 1.
Figure 7B:
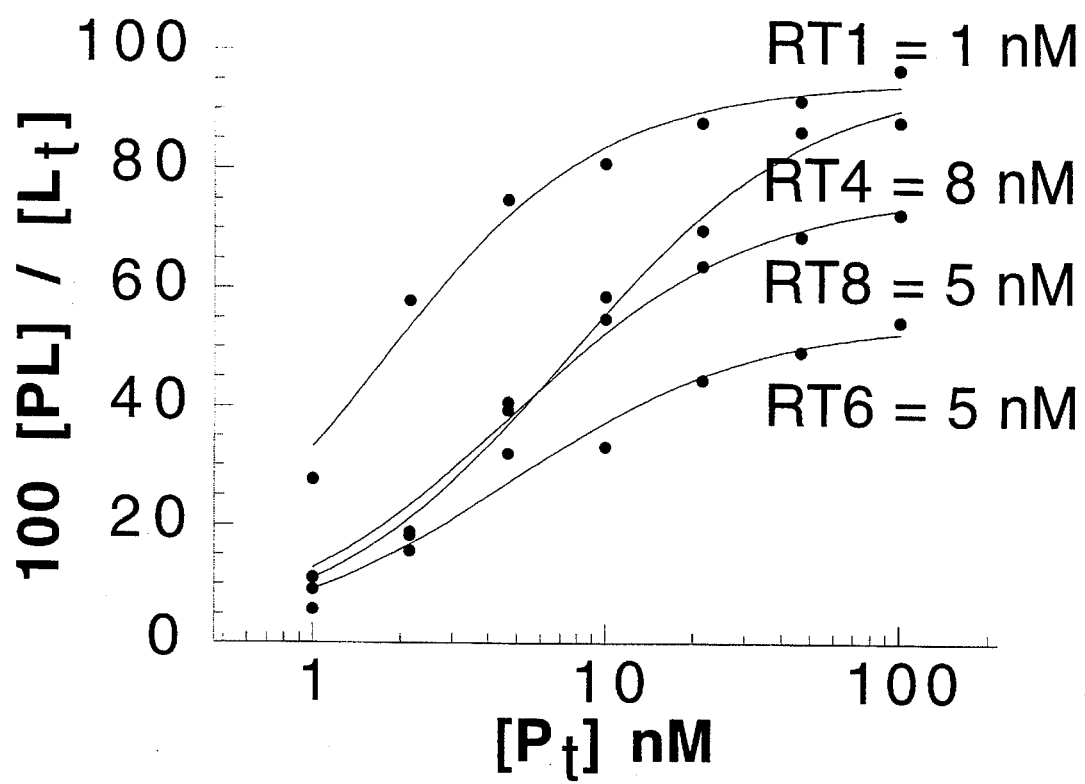
Figure 7C:
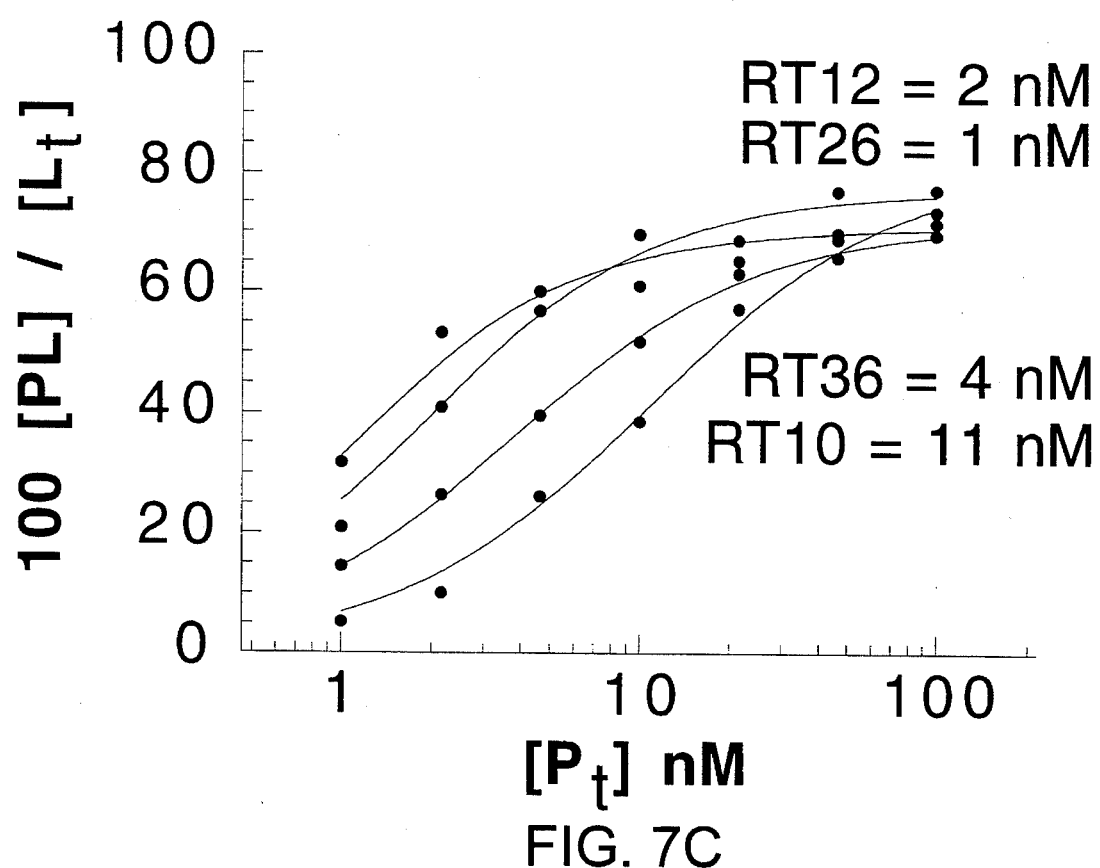
Figure 8:
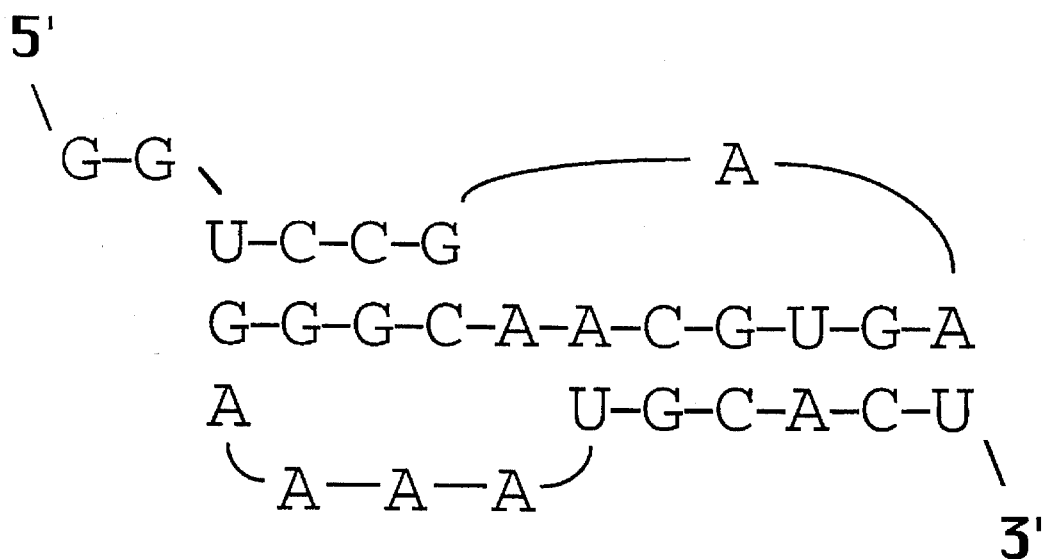
FIG. 8 shows the proposed secondary structure of the RNA pseudoknot inhibitor (SEQ ID NO:73) (Tuerk, C. et al. (1992) Proc. Natl. Acad. Sci., U.S.A. 89:6988–6992).

Affinity values of each of the eight chosen isolates for HIV-1 RT were measured using the filter binding assay described in Example 1 (FIGS. 7A–C). The RNA pseudoknot inhibitor reported in Tuerk, C. et al. (1992) Proc. Natl. Acad. Sci., U.S.A. 89:6988–6992 and U.S. patent application Ser. No. 07/964,624 (see FIG. 8) had an affinity of 5 nM under our conditions, while that of the degenerate library (R0) is 1400 nM. Isolates RT1 (SEQ ID NO:71) and RT26 (SEQ ID NO:44) exhibited the highest affinity having a $K_d$ value of approximately 1 nM, while the others ranged from 2 to 11 nM. Differences in maximum percent bound likely reflect competing ligand structures with lower affinity. No correlation exists between representation in the fully-enriched library (see FIG. 4) and affinity for HIV-1 RT, as ligand RT1 (SEQ ID NO:71) ($K_d$=1 nM), represented once, has a higher affinity than RT6 (SEQ ID NO:57) ($K_d$=5 nM), represented 7 times. Indicated dissociation constants were determined as in Example 1. No significant correlation was observed between the affinity of a molecule and the subset into which it was classified in FIG. 4, as the three highest affinity ligands (RT1 (SEQ ID NO:71), RT12 (SEQ ID NO:48), and RT26 (SEQ ID NO:44) were each classified into different subsets. However, both RT1 (SEQ ID NO:71) and RT26 (SEQ ID NO:44) contain the internal loop structure shown in FIGS. 6A and B, suggesting a possible participation of this motif in conferring high affinity upon ligands that possess it.

Intramolecular Extension Verifies Secondary Structure Predictions.

Figure 9:
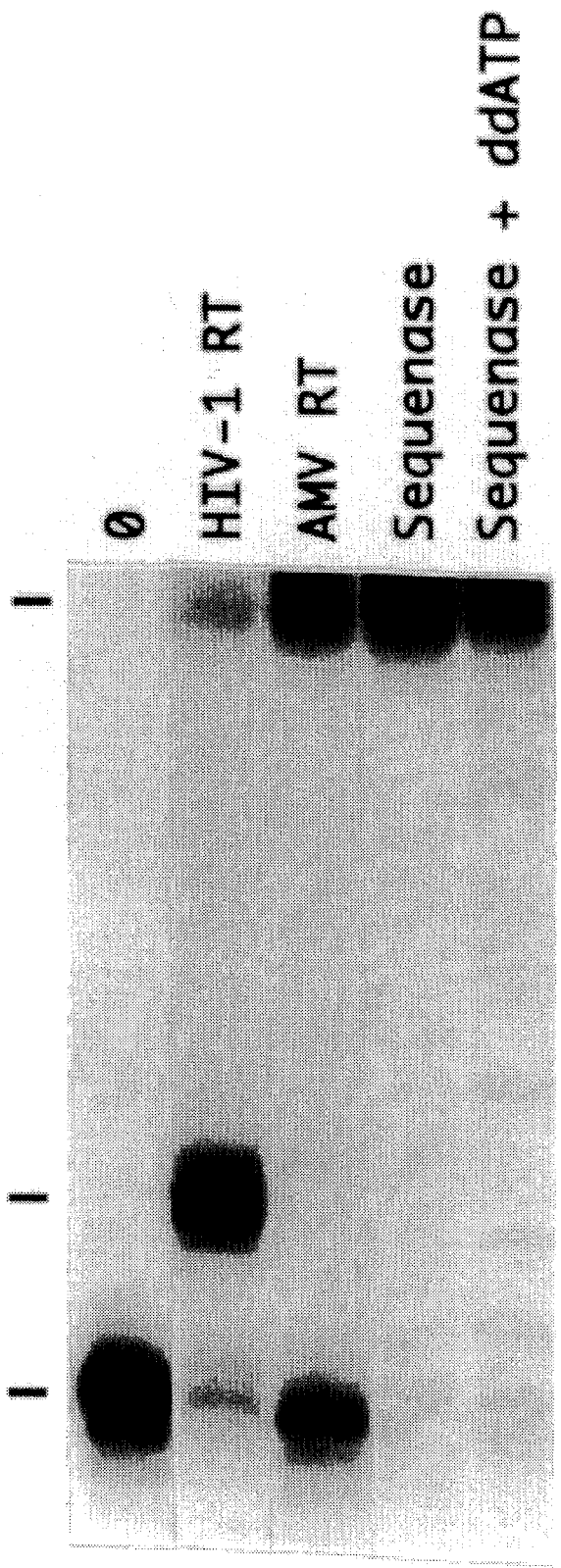
FIG. 9 shows the products of intramolecular extension of RT26 (SEQ ID NO:44). End-labeled RT26 was extended with a saturating concentration of either HIV-1 RT, AMV RT, or Sequenase.
Figure 10F:
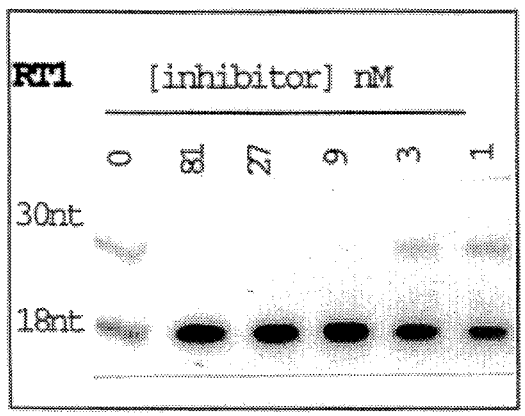
Figure 10G:
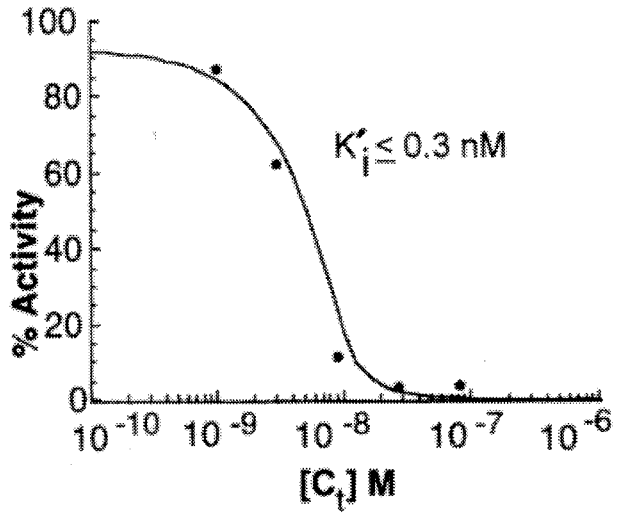
Figure 10H:
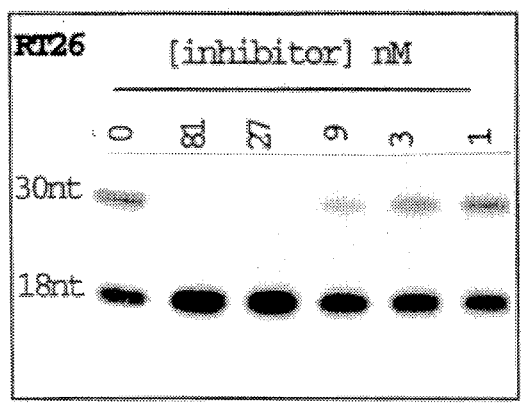
Figure 10I:
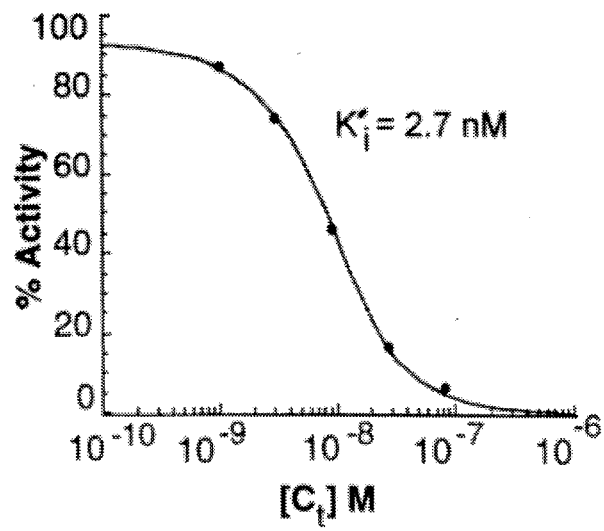

The isolates possessing an intramolecular primer:template junction (RT10 (SEQ ID NO:56), RT12 (SEQ ID NO:48), and RT26 (SEQ ID NO:44)) were assayed for the ability to be extended from their 3' termini by a variety of polymerases. The results for RT26 are shown in FIG. 9. When extended with a saturating concentration of HIV-1 RT, initiation was nearly 100%, while extension proceeded only 5–8 nucleotides before premature termination occurred. AMV-RT initiated only 50%, but extension proceeded to the end of the template. With Sequenase T7 DNA polymerass, both initiation and extension went to completion. The sequence pattern created by extending with Sequenase in the presence of ddATP confirmed the proposed annealing site of the 3' end of RT26 (SEQ ID NO:44). This was also true for RT10 (SEQ ID NO:57) and RT12 (SEQ ID NO:48) (data not shown).

The premature terminations seen when extending RT26 with HIV-1 RT appear to be specific for that enzyme. Both products (premature and complete) were isolated and found to have 100-fold lower affinity for HIV-1 RT than the unextended RT26 (SEQ ID NO:44) (data not shown). HIV-1 RT is less processive than AMV RT and Sequenase, and this lack of processivity might explain the premature termination, although using a saturating concentration of enzyme should have reduced this effect. Two alternative explanations for the premature termination are that addition of the 5–8 templated nucleotides to the 3' end of RT26 (SEQ ID NO:44) creates a low-affinity product, resulting in the release of enzyme more frequently than addition of the next nucleotide, or a trapped product unable to release enzyme or be further extended. Premature termination of RT26 (SEQ ID NO:44) extension occurred within the stem of a potential hairpin, suggesting termination was simply a result of interference by secondary structure; however, similar premature terminations occurred with RT10 (SEQ ID NO:56) and RT12 (SEQ ID NO:48) (data not shown), neither of which occurred at positions stabilized by secondary structure.

A groove on the surface of HIV-1 RT, shown by the X-ray structure to extend from the polymerase catalytic site to the RNase H active site (Kohlstaedt, L. A. et al. (1992) Science 256:1783–1790; Jacobo-Molina, A. et al. (1993) Proc. Natl. Acad. Sci., U.S.A. 90:6320–6324; Arnold, E. et al. (1992) Science 357:85–89; Krug, M. S. and Berger, S. L. (1991) Biochemistry 30:10614–10623), is the best candidate for the protein region contacted by the selected DNA ligands. The ability of RT10 (SEQ ID NO:56) and RT12 (SEQ ID NO:48), and RT26 (SEQ ID NO:44) to be extended demands that the 3' end of these ligands be present in the polymerase active site when they are bound, likely positioned there by interactions between the helix and the protein groove.

Inhibition of Polymerase Activity Suggests Interaction at Substrate Binding Site and/or Active Site.

The ability of each of the 8 isolates to inhibit the RNA-dependent DNA polymerase activity of HIV-1 RT was assayed by measuring the decrease in extension product formation from a primer:template substrate as a function of inhibitor concentration (FIGS. 10A–10E). The substrate for the inhibition assay was a DNA:RNA heteroduplex consisting of an 18 nucleotide end-labeled DNA primer identical in sequence to the 3' end of tRNA$^{Lys,3}$ annealed to a 30 nucleotide RNA template whose sequence matches the genomic primer binding site and the first twelve transcribed nucleotides. Extension reactions were performed as described in Example 1 in the presence of 0, 81, 27, 9, 3, and 1 nM inhibitor as indicated in FIG. 10.

The two bands on the gels are the unextended DNA primer migrating as an 18-mer, and the extended DNA product migrating as a 30-mer. The percent of primer extended as a function of inhibitor concentration is plotted for each inhibitor. $K_i$ values were determined using a least-squares algorithm to fit the data points to Equations 4 and 5 of Example 1. We report these $K_i'$ values rather than true $K_i'$ values because they were not determined with a standard Michaelis-Menten kinetic assay (comparing double-reciprocal plots of reaction velocity as a function of substrate concentration in the presence and absence of inhibitor). However, the correlation between the $K_i'$ and $K_d$ values suggests that the mechanism of inhibition may be a competition between the inhibitory ligand and the substrate for the nucleic acid binding site and/or polymerase active site of RT, although this has not been tested directly.

Almost no inhibition was seen with as high as 81 nM of the degenerate ssDNA library present (R0, $K_i' \geq 3$ μM). The RNA pseudoknot (RNA pk) inhibited the activity of HIV-1 RT with a $K_i'$ value of 4.7 nM under our conditions, consistent with the $K_d$ value shown in FIG. 7 and Tuerk, C. et al. (1992) Proc. Natl. Acad. Sci., U.S.A. 89:6988–6992. The $K_i'$ values of the seven ssDNA ligands assayed (only RT1 (SEQ ID NO:71) and RT26 (SEQ ID NO:44) are shown) were also consistent with the $K_d$ values shown in FIGS. 7A–C. Clones RT1 (SEQ ID NO:71) and RT26 (SEQ ID NO:44) were the most potent inhibitors of the RNA-dependent DNA polymerase activity of HIV-1 RT, having $K_i'$ values of 0.3 nM and 2.7 nM, respectively. The $K_i'$ values of RT4 (SEQ ID NO:64), RT6 (SEQ ID NO:57), RT8 (SEQ ID NO:60), RT10 (SEQ ID NO:56), and RT36 (SEQ ID NO:67) are 4.1 nM, 30 nM, 13 nM, 62 nM, and 6.5 nM, respectively. The $K_i'$ value of RT12 (SEQ ID NO:48) was not calculated. The correlation between the $K_i'$ and $K_d$ values suggests that the mechanism of inhibition may be a competition between the inhibitory ligand and the substrate for the nucleic acid binding site and/or polymerase active site of RT.

EXAMPLE 3

Suicide Inhibitors of HIV-1 RT

The specificity and high affinity for HIV-1 RT exhibited by these ssDNA ligands make them good candidates for suicide inhibitors of HIV-1 RT. This is accomplished by synthesizing a particular ssDNA ligand to HIV-1 RT, incorporating at specific positions nucleotide analogs possessing a reactive group able to covalently crosslink the ligand to HIV-1 RT upon binding. This attachment event would render the enzyme permanently non-functional. Reactive groups are chosen to utilize the specificity of the ligands for HIV-1 RT, being reactive only with HIV-1 RT and only when in close proximity (i.e., only when bound). We have shown that HIV-1 can catalyze addition of a nucleotide to the 3' end of RT10 (SEQ ID NO:56), RT12 (SEQ ID NO:48), and RT26 (SEQ ID NO:44). The ability of the existing HIV-1 RT ligand to extend by addition of a nucleotide to the 3'-end can be exploited for mechanism-based suicide inhibition of the enzyme. This will result in covalent linking of the ligand to the target.

The crucial step in addition of a nucleotide onto the 3'-end of the existing ligand is the abstraction of the proton from the 3'-hydroxyl group by a base associated with the enzyme. Proton extraction or activation of the 3'-hydroxyl aids in the attack of the s-phosphorous of the incoming nucleoside triphosphate. A 3'-terminal nucleoside analog can be designed, that exploits base-activation of the 3'-hydroxyl group to form a reactive intermediate. This species, which is generated in close proximity to the enzyme surface, is then ready to accept an enzyme nucleophile to generate a covalent link.

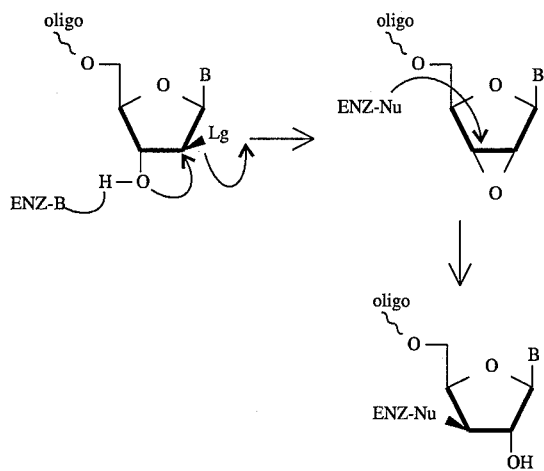

The terminal 3'-nucleotide is modified to bear a leaving group at the 2'-position in anti stereoconfiguration to the 3'-hydroxyl. A typical leaving group could be a halogen, an acetyl group, a sulfonate group, a carbonate group, an acetamide group or any other leaving group. Upon deprotonation of the 3'-hydroxyl by the enzyme a 2',3'-epoxide is formed on the α-face of the nucleoside. This epoxide is labile enough to be attacked from the β-face of the furanose by any adjacent nucleophile on the enzyme. This process results in a covalent link between the enzyme and the ligand.

Figure 15A:
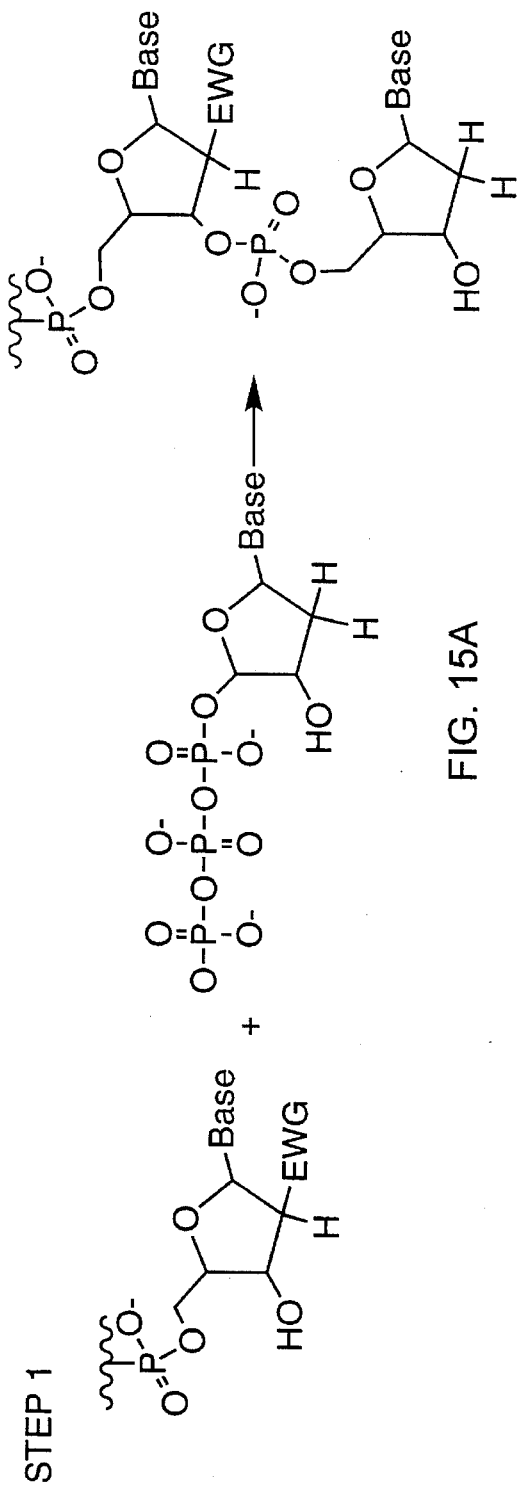
FIGS. 15A–15C show the way in which covalent crosslinking is coupled to the activity of the enzyme. Step 1 shows the catalytic addition of a nucleotide triphosphate to a ligand that has a nucleotide analog at its 3' end containing an electron withdrawing group (EWG) at the 2' carbon. Step 2 shows the spontaneous elimination event whereby the newly added nucleotide is released and yields an electrophilic carbon at the 3' position of the sugar that is stabilized by the electron withdrawing group at the 2' position. Step 3 shows the formation of a covalent crosslink between the protein and the ligand.
Figure 15B:
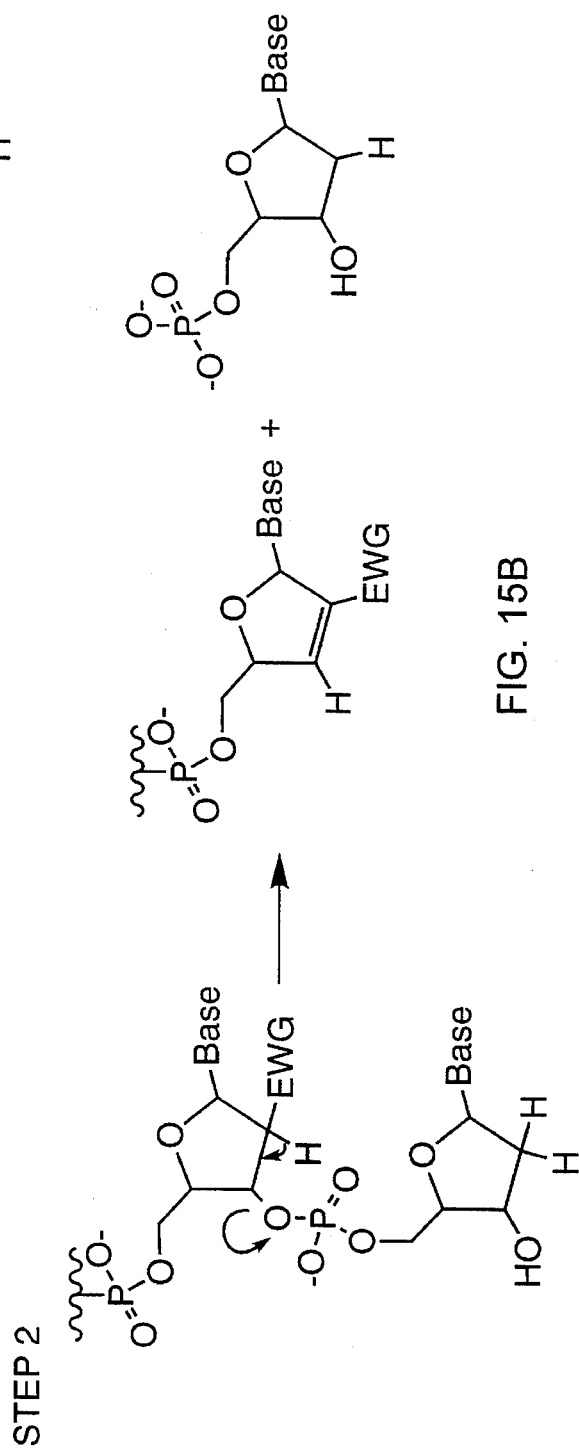
Figure 15C:
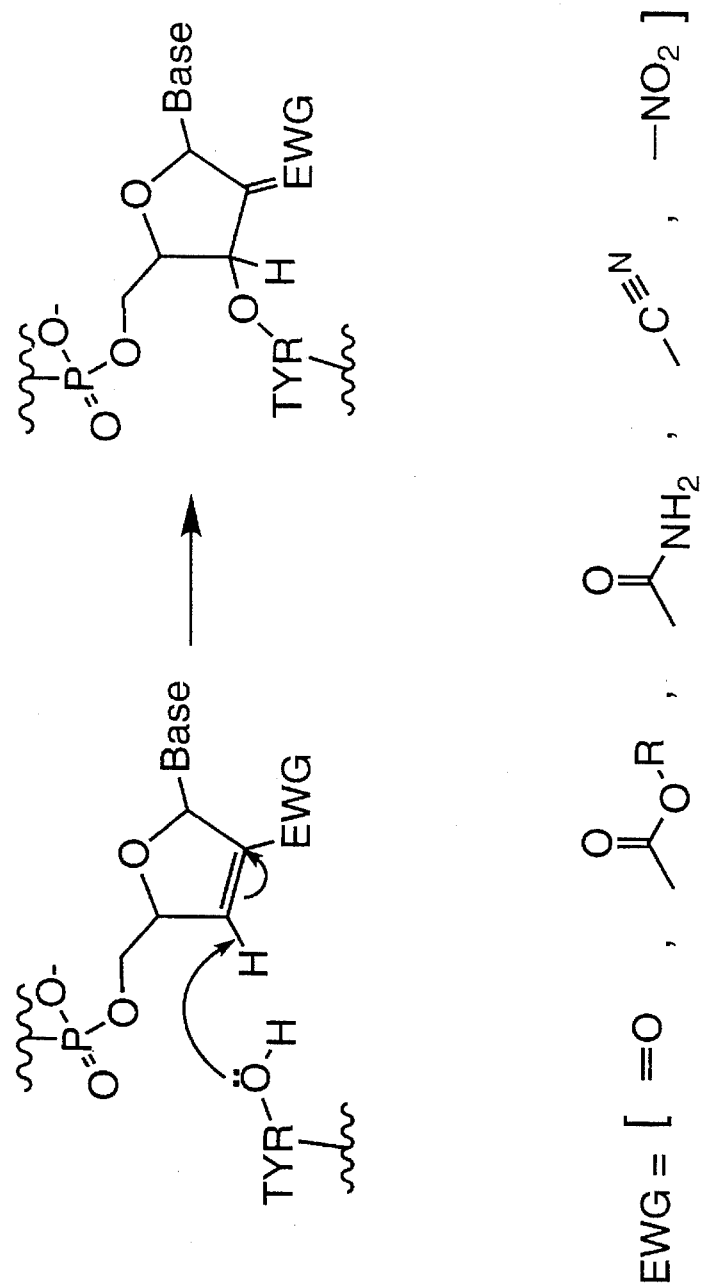

To increase specificity of inhibition, covalent crosslinking could be coupled to activity of the enzyme. If RT10 (SEQ ID NO:56), RT12 (SEQ ID NO:48), and RT26 (SEQ ID NO:44) were synthesized with a nucleotide analog at its 3' end containing an electron withdrawing group at the 2' carbon, catalytic addition of a nucleotide triphosphate (step 1 of FIG. 15) would result in a spontaneous elimination event, releasing the newly added nucleotide and yielding an electrophilic carbon at the 3' position of the sugar polarized by the electron withdrawing group at the 2' position (step 2 of FIG. 15). The reactive 3' carbon would be available for attack by any good nucleophilic group in the vicinity, resulting in the formation of a covalent crosslink between the protein and the ligand (step 3 of FIG. 15). Because this reaction is dependent on catalysis by HIV-1 RT, these inhibitors would specifically target active enzyme. It is possible that RT10 (SEQ ID NO:56), RT12 (SEQ ID NO:48), and RT26 (SEQ ID NO:44)interact with HIV-1 RT in such a way that there are two aspartic acid residues and one tyrosine near enough to perform the reaction.

EXAMPLE 4

Essential Elements of RT1

Biased Synthesis SELEX Identifies Essential Elements of RT1.

Figures 11B, 12A:
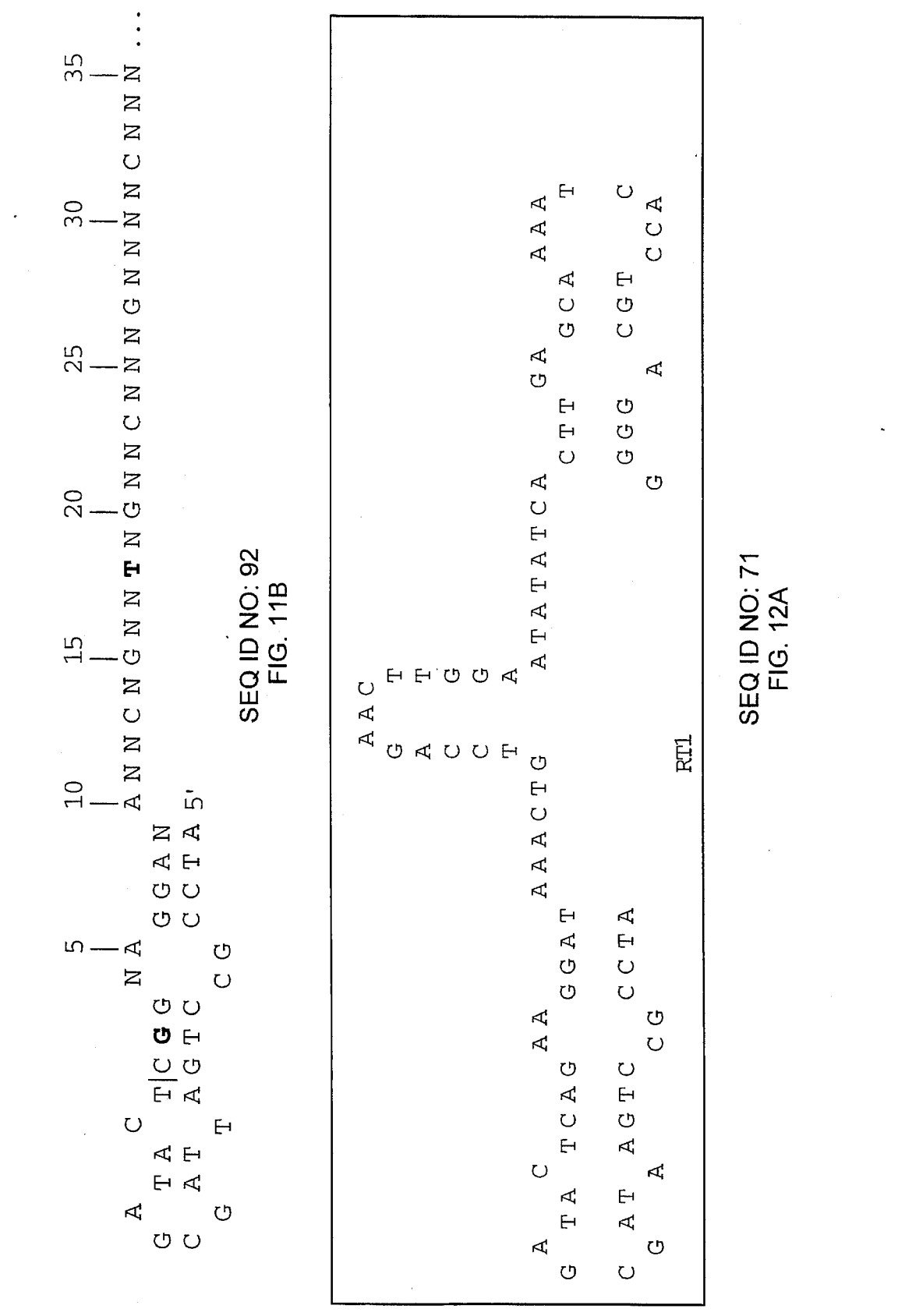

From a library of RT1 mutants, synthesized as described in Example 1, we selected those maintaining a high affinity for HIV-1 RT. In six SELEX cycles the affinity of the library increased almost 1000-fold, from 1500 nM to approximately 2 nM (data not shown). About one half of the 32 isolates had a primary sequence consistent with the predicted secondary structure of RT1 (SEQ ID NO:71), while the other half adopted alternative structures with equally high affinity. The sequences of the isolates similar in structure to RT1 are shown in FIG. 11 (SEQ ID NOS:76–91). The acceptability of mutations varied with position: mutations in the 3' region of the randomized cassette (positions 29–35) were most tolerated, while those in the 5' region (positions 1–7) eliminated ability to bind HIV-1 RT and were selected against. Conservation of positions 1–3 and 6–9 support the internal loop duplex structure comprising the predicted 5' domain of RT1 when paired with the 5' invariant primer-binding region. Additional support for the base-pairing pattern in this domain is provided by the acceptability of the A to G substitution at position 2, which is able to maintain the base pair with the invariant T. The small hairpin predicted to exist in the central domain of RT1 (SEQ ID NO:71) is not supported by the results of this experiment. In the stem of the proposed hairpin, many substitutions disrupting the base-pairing pattern were acceptable, and alternative structures were preferred. No predicted structure could accommodate each of the selected individuals, suggesting the absence of secondary structure in this region. HIV-1 RT might recognize specific unpaired residues of this central domain of RT1, possibly those indicated in the consensus illustrated in FIG. 11B (SEQ ID NO:).

Only 49 Nucleotides Required of RT1 for High Affinity.

Truncated versions of ligand RT1 (SEQ ID NO:71) were synthesized and predicted secondary structures are shown in FIGS. 12A–12C. The predicted secondary structures, (using the RNA folding algorithm of Jaeger, J. A. et al. (1989) Science 244:48–52) were refined by the results of the biased randomization experiment, in particular, the lack of secondary structure in the central region. These truncates were tested for their ability to bind HIV-1 RT with high affinity. RT1t30 (SEQ ID NO:94), composed of the first 30 nucleotides of RT1 containing the internal loop duplex, showed no significant binding below 1 μM HIV-1 RT. However, addition of the next 19 nucleotides, comprising the central stem and loop motif, produced a 49-mer (RT1t49) (SEQ ID NO:93) which bound HIV-1 RT with an affinity of 4 nM, nearly as high as the full-length 81 nucleotide RT1. The relative affinities of RT1 (SEQ ID NO:71), RT1t30 (SEQ ID NO:94), and RT1t49 (SEQ ID NO:93) suggest that all of the specific binding components of RT1 (SEQ ID NO:71) exist in the first 49 nucleotides and that while the internal loop motif is insufficient alone, it likely participates in the interaction with HIV-1 RT in combination with other specific binding components.

49-mer Inhibits HIV-1 RT Specifically.

Figure 13:
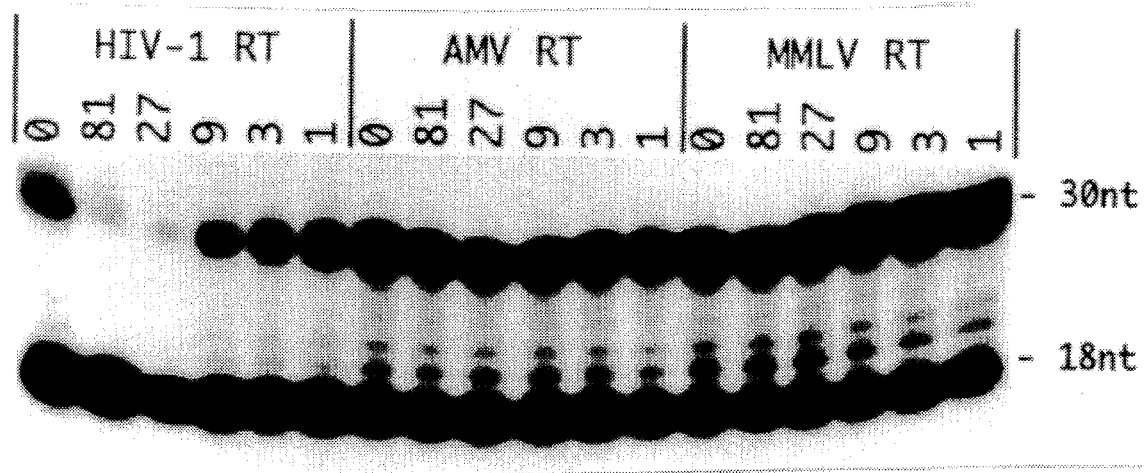
FIG. 13 shows the inhibition specificity assay. Inhibition of the RNA-dependent DNA polymerase activity of three reverse transcriptases (HIV-1 RT, AMV RT, and MMLV RT) was performed as described in Example 1, with inhibitor RT1t49 (SEQ ID NO:93) present at the indicated concentrations in nM.

The inhibition assay described in Example 1 was also used to determine the specificity of inhibition of the RNA-dependent DNA polymerase activity of HIV-1 RT. Using ligand RT1t49 (SEQ ID NO:93) as the competitor, we compared in parallel the ability to inhibit the polymerase activity performed by HIV-1 RT, AMV RT, and MMLV RT. As illustrated in FIG. 13, inhibition of primer extension was seen when performed with HIV-1 RT, but was not detectable when performed with AMV RT and MMLV RT, even at inhibitor concentrations as high as 81 nM. The lack of inhibition of AMV RT and MMLV RT possibly suggests that RT1t49 (SEQ ID NO:93) may have a lower affinity for these enzymes, requiring higher concentrations of RT1t49 (SEQ ID NO:93) to see an inhibitory effect on primer extension.

EXAMPLE 5

RT1 Competes With RNA Pseudoknot for RT Binding

Figure 14:
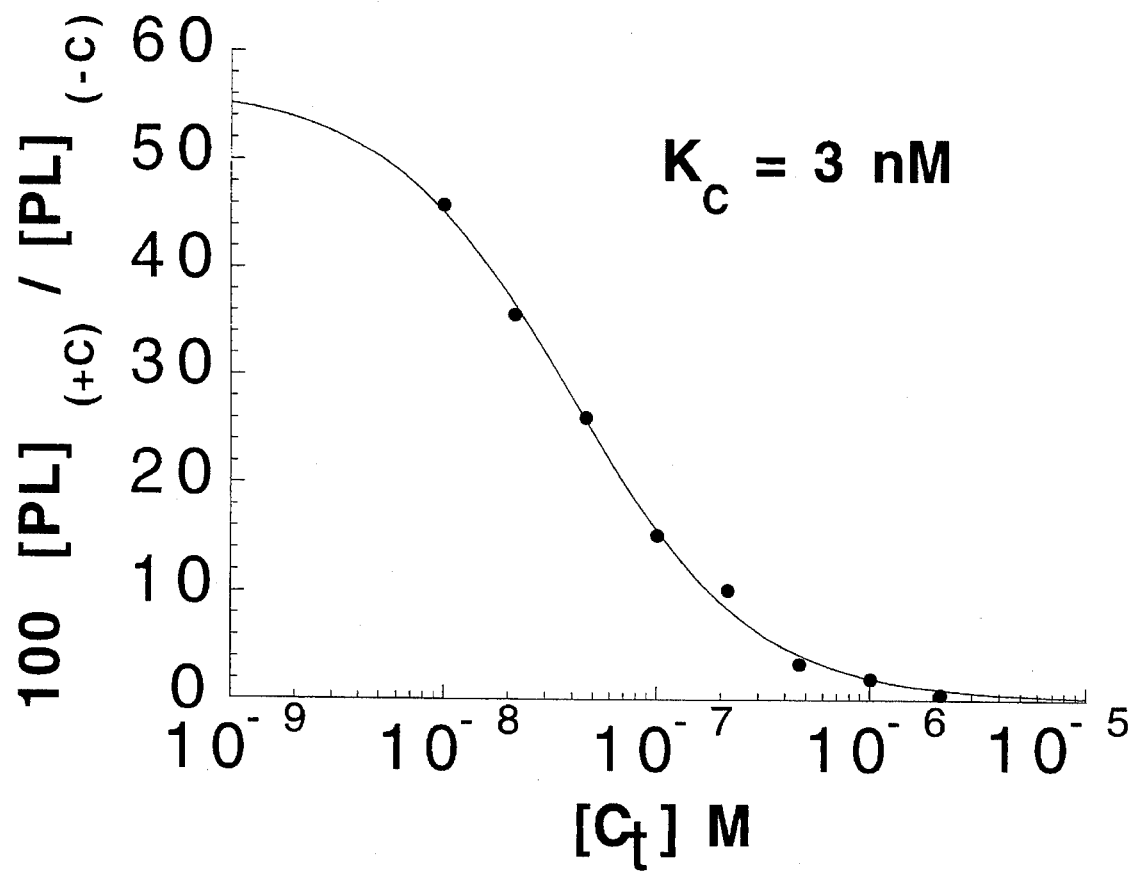
FIG. 14 shows the competitive binding of RT1 (SEQ ID NO:71) and the RNA pseudoknot (RNA pk) (SEQ ID NO:73).

The specific inhibition characteristics exhibited by both an RNA pseudoknot and a ssDNA ligand posed the question of whether two apparently dissimilar molecules, at least at the level of secondary structure, interact with HIV-1 RT at a common nucleic acid binding site. To test this, we measured the ability of the ssDNA ligand RT1 (SEQ ID NO:71) to maintain its specific binding contacts with HIV-1 RT in the presence of high concentrations of RNA pseudoknot (see FIG. 8). FIG. 14 shows the competitive binding of RT1 (SEQ ID NO:71) and the RNA pseudoknot (RNA pk) (SEQ ID NO:73). The percent of RT1 bound in the presence of competitor relative the percent bound in the absence of competitor is plotted as a function of RNA pk concentration. The $K_c$ value for RNA pk (3 nM) was determined using an algorithm that fit the data points to Equations 4 and 5 in Example 1, and was consistent with the Kd value (5 nM) measured using the nitrocellulose filter binding assay described in Example 1. As shown graphically in FIG. 14, when a stoichiometric equivalent of RNA pk was added, approximately one half of the complexed RT1 was displaced, and nearly all was displaced when a large excess of RNA was added. These results leave little doubt that binding of RT1 (SEQ ID NO:71) and RNA pk (SEQ ID NO:73) to HIV-1 RT are mutually exclusive. However, with this assay we are unable to distinguish between an interaction of both ligands at a common site or an interaction of each at different sites, with a conformational change upon binding the first that prevents subsequent binding of the second.

---

We claim:

1. A method of identifying nucleic acid ligands to HIV-1 reverse transcriptase, comprising:
   a) preparing a candidate mixture of deoxyribonucleic acids (DNA);
   b) contacting the candidate mixture of DNA with HIV-1 reverse transcriptase, wherein nucleic acids having an increased affinity to HIV-1 reverse transcriptase relative to the candidate mixture may be partitioned from the remainder of the candidate mixture;
   c) partitioning the increased affinity nucleic acids from the remainder of the candidate mixture; and
   d) amplifying the increased affinity nucleic acids to yield a ligand-enriched mixture of nucleic acids, whereby nucleic acid ligands to HIV-1 reverse transcriptase may be identified.

2. The method of claim 1 further comprising:
   (e) repeating steps b), c) and d).

3. The method of claim 1 wherein said candidate mixture of DNA is comprised of single stranded DNA.

\* \* \* \* \*